(12) United States Patent
Chelvam et al.

(10) Patent No.: US 11,427,596 B2
(45) Date of Patent: Aug. 30, 2022

(54) METAL-FREE SOLVENT-FREE SYNTHESIS OF FUSED-PYRIDO HETEROCYCLES AND BIOMEDICAL APPLICATIONS

(71) Applicant: Indian Institute of Technology Indore, Simrol (IN)

(72) Inventors: Venkatesh Chelvam, Simrol (IN); Premansh Dudhe, Khandwa (IN); Mena Asha Krishnan, Indore (IN); Avinash Sonawane, Indore (IN)

(73) Assignee: INDIAN INSTITUTE OF TECHNOLOGY INDORE, Indore (IN)

( * ) Notice: Subject to any disclaimer, the term of this patent is extended or adjusted under 35 U.S.C. 154(b) by 0 days.

(21) Appl. No.: 16/931,838

(22) Filed: Jul. 17, 2020

(65) Prior Publication Data
US 2021/0070765 A1    Mar. 11, 2021

(30) Foreign Application Priority Data
Jul. 19, 2019   (IN) .............................. 201921029311

(51) Int. Cl.
| | |
|---|---|
| *C07D 491/048* | (2006.01) |
| *A61P 31/04* | (2006.01) |
| *A61P 35/00* | (2006.01) |
| *C07D 471/04* | (2006.01) |

(52) U.S. Cl.
CPC .......... *C07D 491/048* (2013.01); *A61P 31/04* (2018.01); *A61P 35/00* (2018.01); *C07D 471/04* (2013.01)

(58) Field of Classification Search
CPC ... C07D 491/048; C07D 471/04; A61P 31/04; A61P 35/00
See application file for complete search history.

(56) References Cited

PUBLICATIONS

Dassonneville, B., "[2+ 2+ 2] Cycloadditions of alkynylynamides—A total synthesis of perlolyrine and the first total synthesis of "isoperlolyrine"." (2011): 2836-2844.*

* cited by examiner

*Primary Examiner* — John M Mauro

(57) ABSTRACT

Embodiments herein provide fused-pyrido heterocycles such as azaindoles, carboline derivatives, furo[b]pyridines or furo[b]pyridine-isatin hybrids of Formula I.

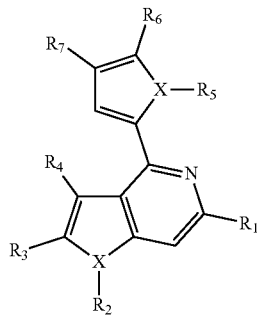

Formula I

Embodiments also relate to a process for a synthesis of variety of complex pyrido-heterocycles The pyrido-heterocycles can be used for treating cancer (cervix, kidney, lung, breast and epidermal skin) and multi-drug resistant tuberculosis. These heterocycles can also be used as anti-biofilm agents against pathogenic strains, which will minimize the risk of secondary infections.

14 Claims, 16 Drawing Sheets

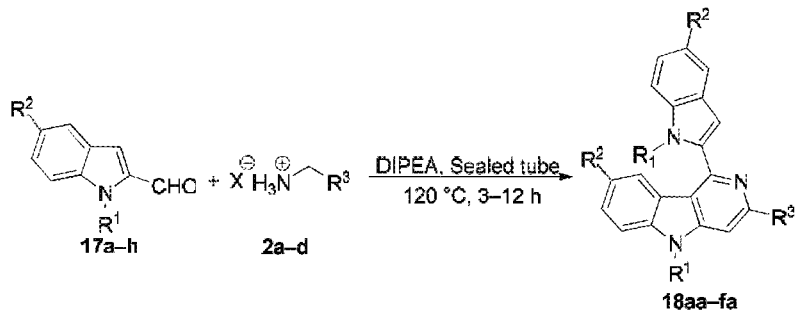

17a; R¹ = Me, R² = H
17b; R¹ = Bn, R² = H
17c; R¹ = Me, R² = MeO
17d; R¹ = p-MeOBn, R² = H
17e; R¹ = ⁿBu, R² = H
17f; R¹ = Ts, R² = H
17g; R¹ = Me, R² = Br
17h; R¹ = Boc, R² = H

2a; R³ = COOMe, X = Cl
2b; R³ = COOEt, X = Cl
2c; R³ = COOᵗBu, X = Cl
2d; R³ = CN, X = HSO₄

18aa; R¹ = Me, R² = H, R³ = COOMe; 70%
18ab; R¹ = Me, R² = H, R³ = COOEt; 66%
18ac; R¹ = Me, R² = H, R³ = COOᵗBu; 67%
18ba; R¹ = Bn, R² = H, R³ = COOMe; 58%
18bb; R¹ = Bn, R² = H, R³ = COOEt; 51%
18bc; R¹ = Bn, R² = H, R³ = COOᵗBu; 47%
18ca; R¹ = Me, R² = MeO, R³ = COOMe; 72%
18da; R¹ = p-MeOBn, R² = H, R³ = COOMe; 60%
18ea; R¹ = R¹ = ⁿBu, R² = H, R³ = COOMe; 45%
18fa; R¹ = Ts, R² = H, R³ = COOMe; 54%
18ga; R¹ = Me, R² = Br, R³ = COOMe; 0%
18ha; R¹ = Boc, R² = H, R³ = COOMe; 0%

FIG. 9

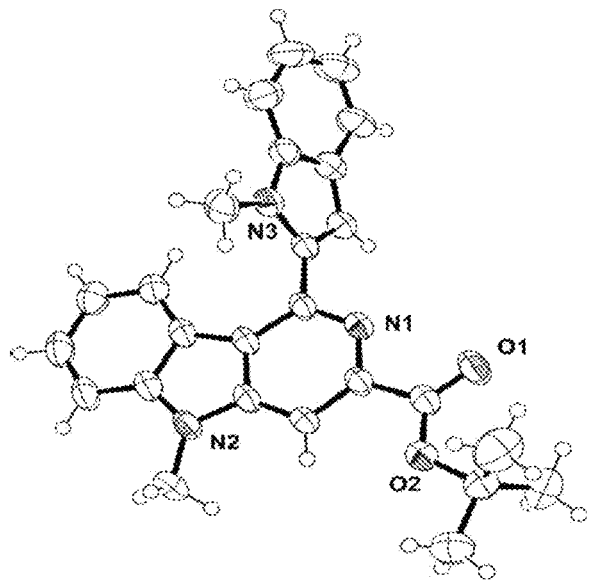

FIG. 10

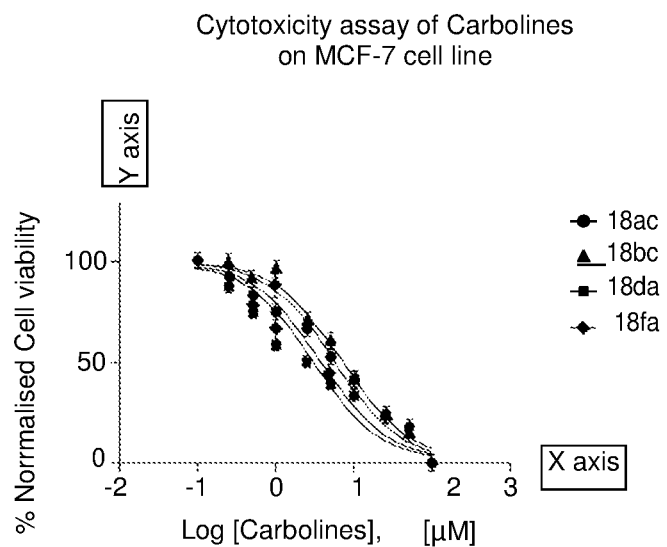
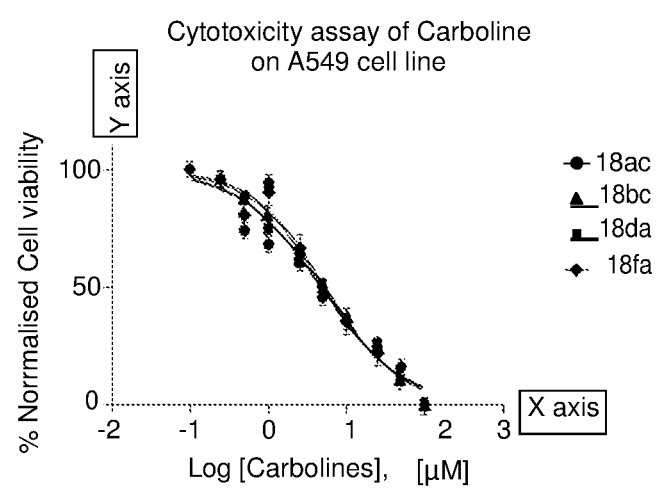
FIG. 16 (CONT'D)

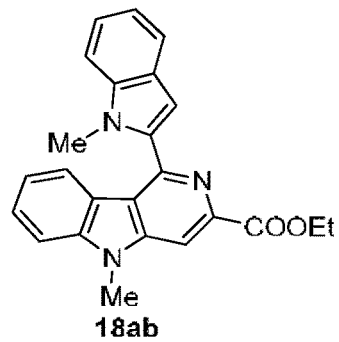
18ab
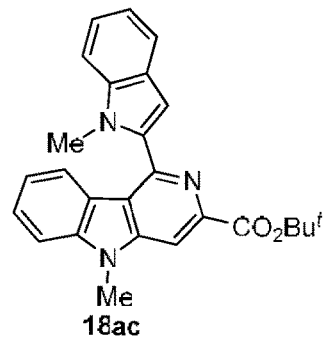
18ac
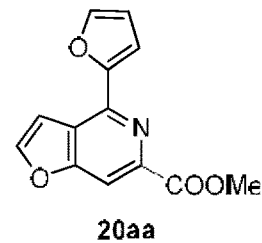
20aa
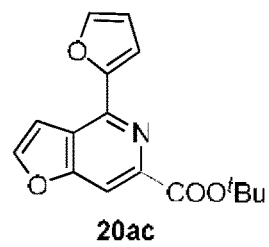
20ac
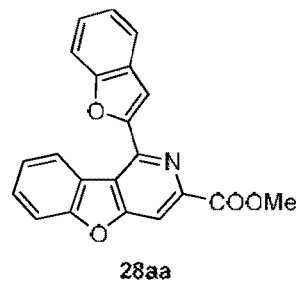
28aa
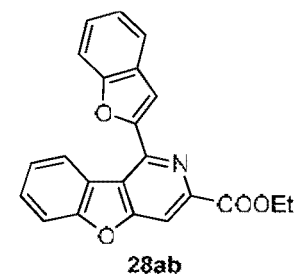
28ab
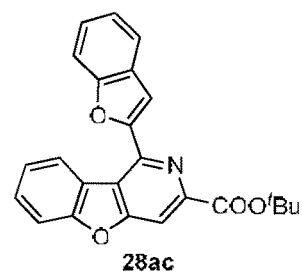
28ac
FIG. 18 (CONT'D)

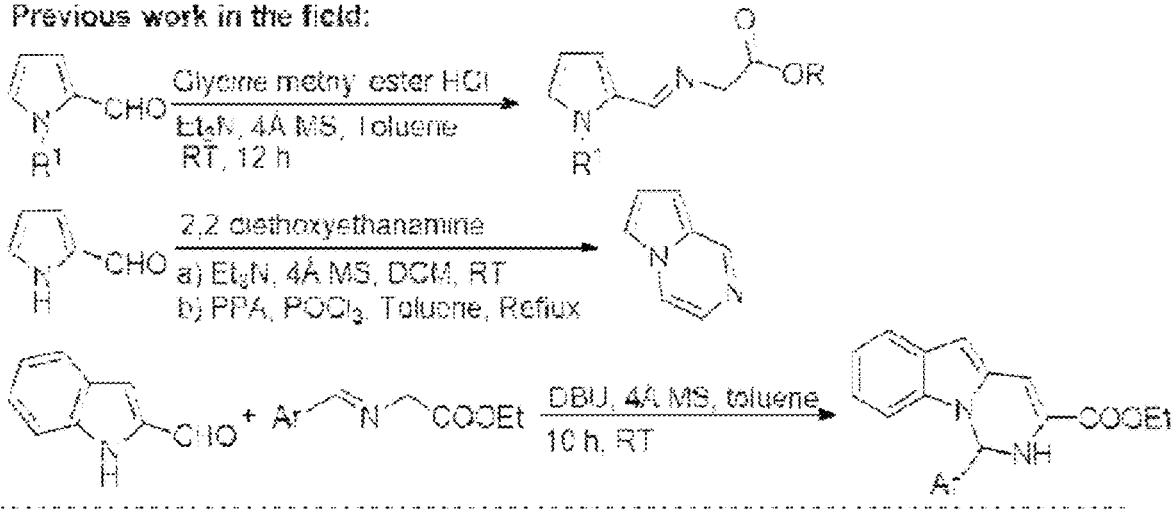
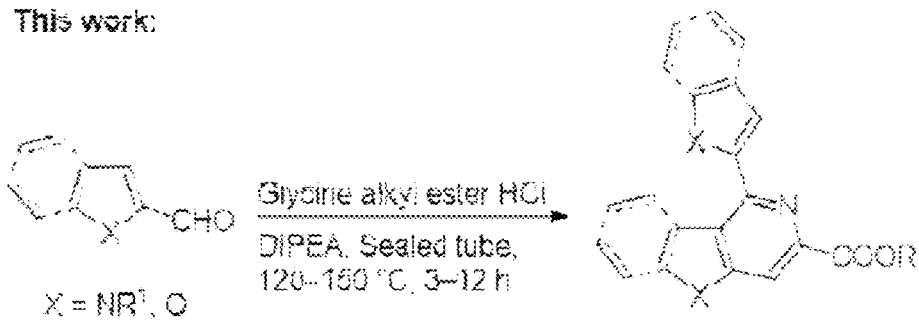
FIG. 19

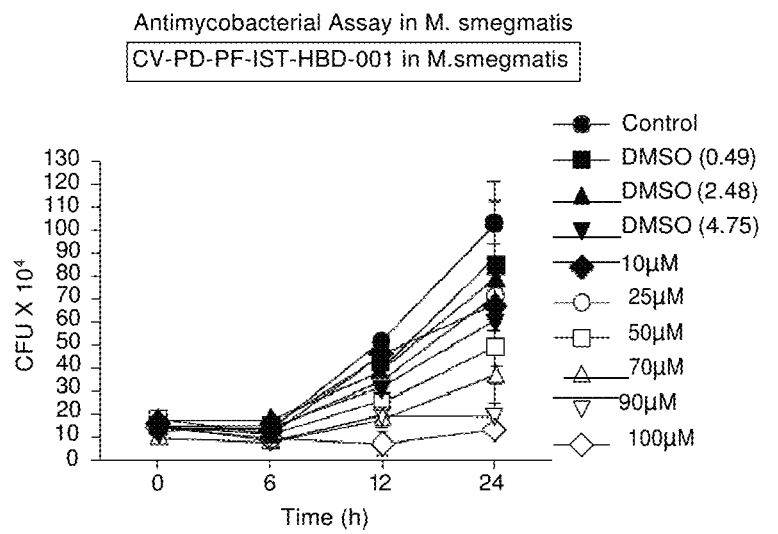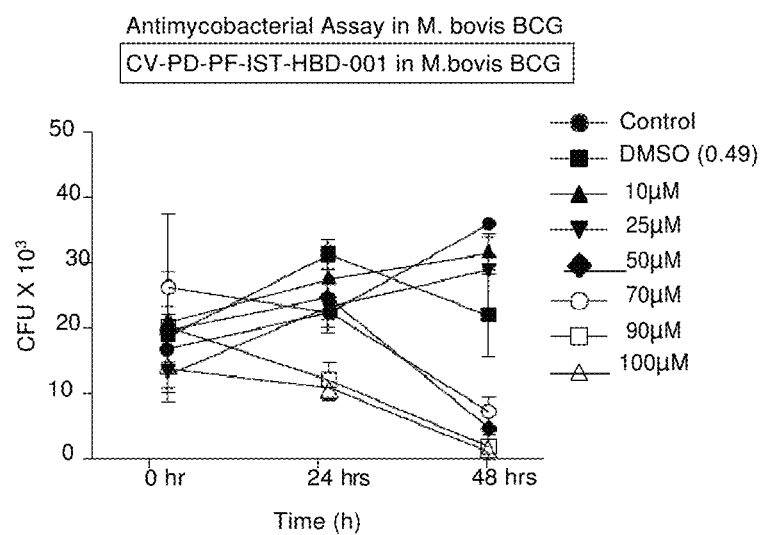
FIG. 20

METAL-FREE SOLVENT-FREE SYNTHESIS OF FUSED-PYRIDO HETEROCYCLES AND BIOMEDICAL APPLICATIONS

FIELD OF INVENTION

The present invention relates to a method and system for metal-free solvent-free synthesis of fused-pyrido heterocycles and its applications to treat cancer and tuberculosis. The present application is based on, and claims priority from an Indian Application Number 201921029311 filed on 19 Jul. 2019 the disclosure of which is hereby incorporated by reference herein.

BACKGROUND

Fused pyridine compounds belong to the largest family of alkaloids, and these are extensively distributed in nature, including plants, marine organisms, insects, mammalians as well as human tissues and body fluids. These heterocycles are of great interest due to their diverse set of biological activities. They act as a specific ligand for a particular protein and by cautious modulation of protein expression with the help of these external ligands (agonist and antagonists), significant biological functions can be manipulated. Therefore, it is pertinent in the field of chemical biology to look for appropriate protein-ligand interaction for every newly discovered molecule. Structural analogy of newly synthesized molecules with the already existing (known) ligands may become a vital tool to solve this riddle.

Azaindoles (pyrrollopyridines) are closest bioisosteres of indoles and purines. Hence, they play indispensable role in mimicking the natural ligand-target interactions. Therefore, pyrrollopyridines have become an integral core unit in many important drug candidates developed in recent times. However, their synthesis has always been a great challenge for synthetic chemists. Due to electron deficient nature of pyridine ring, classical indole synthesis including Fischer and Madelung cyclization often cannot be effectively applied to the synthesis of the corresponding azaindoles. Also, conventionally developed protocols aren't harvested sufficiently in the pharmaceutical industries as the presence of any heavy metals in the synthetic strategy may cause unwanted toxicity and inaccuracy in the biological studies.

Indolopyridines (carbolines) widely attributed to their DNA intercalating properties, enzyme inhibition properties (mainly CDK, topoisomerase, and monoamine oxidase) and interaction with benzodiazepine receptors and 5-hydroxy serotonin receptors. Furthermore, these compounds have demonstrated a broad spectrum of pharmacological properties including sedative, anxiolytic, hypnotic, anticonvulsant, antitumor, antiviral, antiparasitic as well as antimicrobial activities. Although, the synthesis of tailored carboline derivatives still remains an unsolved mystery to synthetic chemists. The overall assessment of existing protocols reveals severe issues of poor yield, limited substrate scope including use of very specific set of starting materials, involvement of extreme thermal conditions, corrosive reagents and toxic heavy metal catalysts.

Over the last two decades, the furopyridines have been extensively studied as bio-isosteres of indoles. Hence, these heterocycles have emerged as useful pharmacophores in several therapeutic areas such as treatment of cognitive or autoimmune disorders, migraine, irritable bowel syndrome, and asthma. Benzofuropyridine, another intriguing member of the fused pyridine class has also found attention-grabbing applications in pharmaceutical and OLED industry. However, the scope of further developments in the synthetic procedures have remained restricted due to limited substrate scope and lack of innovative approaches. The existing protocols, majorly rely on expensive heavy metal catalysts, and are limited to furan ring synthesis over substituted pyridine derivatives. The alternative approach involving the formation of the pyridine nucleus over a furan derivative has not been thoroughly investigated.

To summarize the challenges with the state-of-the-art methods, standard indole and carbazole synthesis protocols don't work in the domain due to innate structural complexities. The pyridine ring is very much electron-deficient in comparison to the benzene counterparts. This has limited the scope of five-membered ring formation over the pyridine rings. Moreover, the nitrogen-containing six-membered ring formation on pyrroles and indoles have not been studied thoroughly to devise novel methodologies in the area due to narrow substrate scope. Also, the thermal stability of pyrrole and indole derivatives also confines their use as starting materials. Further, methodologies with narrow substrate scope, expensive starting materials, heavy metal catalysts, and tedious work-up procedures are difficult to commercialize because these elements are not cost-effective at large scale productions. Furthermore, conventional methods employ metal catalysts and organic solvents are extensively used in organic synthesis and due to their inborn toxicity and environmental hazards, they are a matter of much concern.

To overcome the above drawbacks, a versatile one-pot approach to synthesize a whole range of substituted azaheterocycles has been designed and developed herein. The novel synthetic protocol is a metal-free and solvent-free method to obtain variety of compounds only by strategic design of starting materials. The synthesized compounds are carefully screened and found to possess interesting biological activities or efficacy as anti-cancer, anti-mycobacterial, and anti-biofilm compounds. The compounds synthesized by the present invention circumvents the need for complex purification procedures or expensive sophisticated equipment.

OBJECT OF INVENTION

The principal object of the embodiments herein is to provide for fused pyrido-heterocycles.

Another object of the present invention is to provide a method for metal-free solvent-free synthesis of fused-pyrido heterocycles.

Yet another object of the embodiments herein is to synthesize compounds that have biological efficacy against cancer and multi-drug resistant pathogens.

SUMMARY

Accordingly, the embodiments herein provide a fused-pyrido heterocycles, and process of preparation thereof. The pyrido-heterocycles of the present invention can be used for treating cancer (cervix, kidney, lung, breast and epidermal skin) and multi-drug resistant tuberculosis. These heterocycles can also be used as anti-biofilm agents against pathogenic strains, which will minimize the risk of secondary infections.

In an embodiment, the fused-pyrido heterocycles such as azaindoles, carboline derivatives, furo[b]pyridines or furo[b]pyridine-isatin hybrids of the present invention are compounds of Formula I

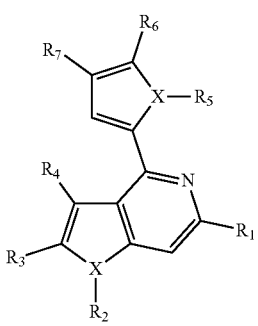

Formula I and its prodrug, stereoisomer, racemate, salt, hydrate, salt hydrate, acid salt hydrate, solvate, an isomorphic crystalline form, and compositions thereof;

wherein, 'X' is one of nitrogen or oxygen;

$R_1$ is one of morpholino methanone, —CONH$_2$, —CN, —CHO, —COOH, —ROH, —COOR wherein R is an alkyl group $R_2$ and $R_5$ is at least one independently selected from a group consisting of —H, -Boc, alkyl, tosyl, phenyl sulfonyl, aryloxy, benzyloxy, optionally substituted benzyl, and optionally substituted aryl; and $R_3$, $R_4$, $R_6$ and $R_7$ is at least one independently selected from —H, alkyl group, or $R_3$ and $R_4$, and $R_6$ and $R_7$, may be fused to form an optionally substituted benzene ring.

In another embodiment, the present invention also provides for a process for preparation of the fused-pyrido heterocycles, the process steps comprising: contacting a reactant selected from a group consisting of N-substituted pyrrole-2-carboxaldehyde, N-substituted indole-carboxaldehyde, optionally substituted furfural, and benzofuran-2-carboxaldehyde with an acid salt of glycine alkyl ester in the presence of a base at a temperature range of 100-160° C. for a period of 3-15 hours to obtain the compound of Formula I.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

This method and system is illustrated in the accompanying drawings, throughout which like reference letters indicate corresponding parts in the various figures. The embodiments herein will be better understood from the following description with reference to the drawings, in which:

FIG. 9 illustrates synthesis of γ-carbolines 18aa-fa, according to the embodiments as disclosed herein;

FIG. 10 illustrates Single crystal XRD analysis for γ-carboline derivative 18ac (CCDC: 1897787), according to the embodiments as disclosed herein;

FIG. 19 illustrates key features of the invention that differentiates the invention from existing protocols, according to the embodiments as disclosed herein.

FIG. 20 illustrates in vitro antituberculosis activity of furo[b]pyridine-isatin hybrid derivative 26 against *Mycobacterium smegmatis* (50-100 μM); SD (n=3) and multidrug resistant/opportunistic *Mycobacterium bovis* (70-100 μM); SD (n=3), according to the embodiments as disclosed herein

DETAILED DESCRIPTION OF INVENTION

Figure 1:
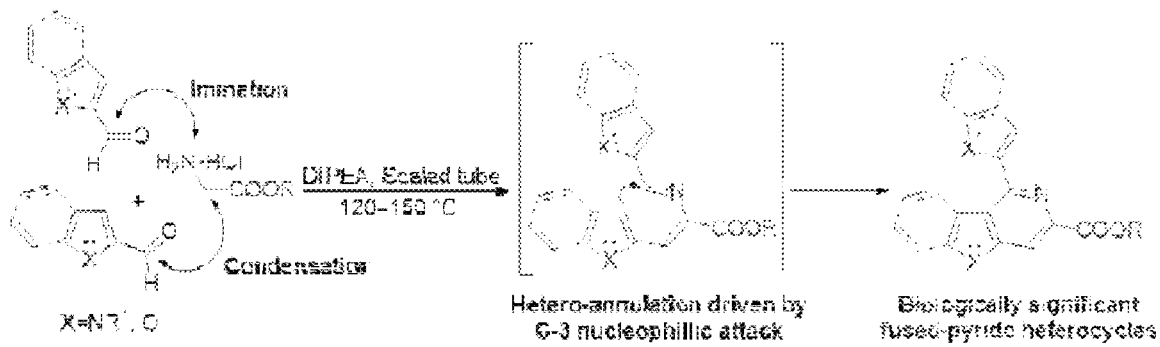
FIG. 1 illustrates a schematic representation of invention, according to the embodiments as disclosed herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

The term "alkyl" as used herein includes a chain of carbon atoms, which is optionally branched.

The term "aryl" as used herein includes molecular fragments or radicals comprising an aromatic mono or polycyclic ring of carbon atoms, such as phenyl, naphthyl, and the like.

The term "substituted aryl" as used herein includes molecular fragments or radicals comprising aryl with one or more substituents, such as alkyl, heteroalkyl, halo, hydroxy, amino, alkyl or dialkylamino, alkoxy, alkylsulfonyl, aminosulfonyl, carboxylate, alkoxycarbonyl, aminocarbonyl, cyano, nitro, and the like. It is to be understood that the alkyl groups in such substituents may be optionally substituted with halo.

The invention described herein pertains to discovery of fused-pyrido heterocycles such as substituted 5-azaindoles, γ-carbolines, furo[b]pyridines, 5-azaindole or furo[b]pyridine-isatin hybrids, benzofuropyridines and their chalcogenic counterparts. The compounds of the present invention find valuable application in treating cancer [HeLa (cervical), MCF-7 (breast), HEK293 (kidney), A431 (squamous cervical) and A549 cells (lung)] and multi-drug resistant pathogens such as agents that cause tuberculosis (*Mycobacterium smegmatis, Mycobacterium bovis* (BCG) and other virulent tuberculosis causing strains. The compounds of the present invention can also be used for anti-biofilm activity against a panel of biofilm forming bacteria or pathogens. The present invention also describes a convenient process for the synthesis of fused-pyrido heterocycles. The method is general for obtaining a variety of heterocycles in a simple one-pot single step methodology. The purification of the products is easy, and yields are reproducible.

The invented methodology herein, describes a simple one pot synthesis for a library of pyridofuran derivatives. Moreover, a panel of isatin hybrids of novel pyridofurans with isatin binding was developed in our laboratory and shown to exhibit anti-mycobacterial efficacy against both non-virulent and virulent mycobacterium strains that causes tuberculosis. In addition, several novel pyridofuran molecules and their functional derivatives were investigated for their anti-TB properties and exhibit antituberculosis activity against multidrug resistant *Mycobacterium* strains.

The invented synthetic methodology has been successfully optimized to produce a wide range of heterocycles in decent yields via a simplified one-pot protocol, which are otherwise can be prepared only by multi-step synthesis with very limited yields.

In an embodiment of the present invention, the fused-pyrido heterocycles such as azaindoles, carboline derivatives, furo[b]pyridines are compounds of Formula I

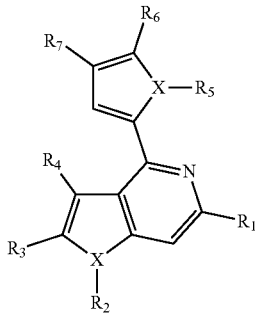

Formula I and its prodrug, stereoisomer, racemate, salt, hydrate, salt hydrate, acid salt hydrate, solvate, an isomorphic crystalline form, and compositions thereof;

wherein, 'X' is one of nitrogen or oxygen;

$R_1$ is one of morpholino methanone, —CONH$_2$, —CN, —CHO, —COOH, —ROH, —COOR wherein R is an alkyl group $R_2$ and $R_5$ is at least one independently selected from a group consisting of —H, -Boc, alkyl, tosyl, phenyl sulfonyl, aryloxy, benzyloxy, optionally substituted benzyl, and optionally substituted aryl; and $R_3$, $R_4$, $R_6$ and $R_7$ is at least one independently selected from —H, alkyl group, or $R_3$ and $R_4$, and $R_6$ and $R_7$, may be fused to form an optionally substituted benzene ring.

In another embodiment, the present invention discloses compounds of Formula I, wherein X is nitrogen; $R_1$ is one of morpholino methanone, —CONH$_2$, —CN, —CHO, —COOH, —ROH, and —COOR wherein R is an alkyl group selected from a group consisting of -Me, Et, or $^t$Bu; $R_2$ and $R_5$ are identical and are selected from a group consisting of hydrogen, methyl, benzyl, methoxy benzyl, tosyl, and phenyl sulfonyl; and $R_3$, $R_4$, $R_6$ and $R_7$ is one independently selected from —H, or —CH$_3$.

In yet another embodiment, the present invention discloses compounds of Formula I, wherein X is nitrogen; $R_1$ is one of morpholino methanone, —CONH$_2$, —CN, —CHO, —COOH, —ROH, and —COOR wherein R is an alkyl group selected from a group consisting of -Me, Et, or $^t$Bu; $R_2$ and $R_5$ are identical and are selected from a group consisting of hydrogen, methyl, benzyl, methoxy benzyl, tosyl, and phenyl sulfonyl, $R_3$ and $R_4$, and $R_6$ and $R_7$, may be fused to form an optionally substituted benzene ring.

In another embodiment, the compound of Formula I includes

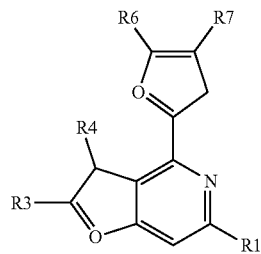

wherein $R_1$ is —COOR wherein R is an alkyl group selected from a group consisting of -Me, Et, or $^t$Bu; $R_3$, $R_4$, $R_6$ and $R_7$ is at least one independently selected from —H, alkyl group, or $R_3$ and $R_4$, and $R_6$ and $R_7$, may be fused to form an optionally substituted benzene ring.

In another embodiment, the present invention discloses compounds of Formula II

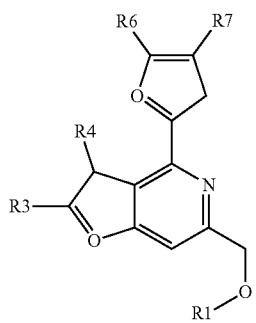

Formula II and its prodrug, stereoisomer, racemate, salt, hydrate, salt hydrate, acid salt hydrate, solvate, an isomorphic crystalline form, and compositions thereof; wherein, R1 is an optionally substituted isatin, R3, R4, R6 and R7 is at least one independently selected from —H, alkyl group, or R3 and R4; and R6 and R7, may be fused to form an optionally substituted benzene ring.

In an embodiment, the compound of Formula II is

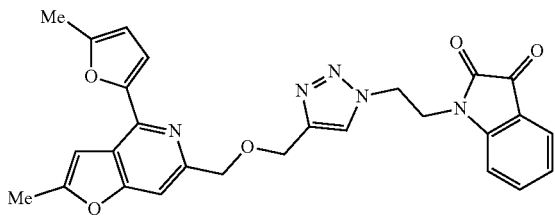 [SMILES: Cc1ccc(-c2nc(COCc3cn(CCN4C(=O)C(=O)c5ccccc54)nn3)cc3oc(C)cc23)o1]

The present invention also describes a convenient process for preparation of the compounds of Formula I and II. In an embodiment, the compounds of Formula I may be prepared by contacting a reactant selected from a group consisting of N-substituted pyrrole-2-carboxaldehyde, N-substituted indole-carboxaldehyde, optionally substituted furfural, and benzofuran-2-carboxaldehyde with an acid salt of glycine alkyl ester in the presence of a base (selected from N,N-Diisopropylethylamine (DIPEA), triethylamine (Et$_3$N), K$_2$CO$_3$, NAH, Cs$_2$CO$_3$, and 1,8-Diazabicyclo[5.4.0]undec-7-ene (DBU) at a temperature range of 100-160° C. for a period of 3-15 hours to obtain the compound of Formula I. In said embodiment, the molar ratio of the reactant to the acid salt of glycine alkyl ester is in the range of 1:2 to 2:1, preferably 2:1, and the molar ratio of the reactant to the base is in the range of 1:1 to 1:15, preferably in the range of 1:1 to 1:2.

The present invention also discloses a process for preparation of compounds of Formula II. The process comprises the steps of contacting an optionally substituted furfural with an acid salt of glycine alkyl ester in the presence of a base (selected from N,N-Diisopropylethylamine (DIPEA), triethylamine (Et$_3$N), K$_2$CO$_3$, NAH, Cs$_2$CO$_3$, and 1,8-Diazabicyclo[5.4.0]undec-7-ene (DBU) at a temperature range of 100-160° C. for a period of 3-15 hours to obtain the compound of Formula I; b) reacting the compound of Formula I in the presence of a reducing agent (LiAlH$_4$) in THF under first reaction conditions (a temperature range of 0°C-30°C for a period of 10-30 minutes) to yield a corresponding alcohol; c) propargylation of the corresponding alcohol obtain in step a) with propargyl bromide and sodium hydride in refluxing anhydrous THF in the presence of a catalyst (tetrabutylammonium iodide (TBAI)) under second reaction conditions (2-4 hours) to obtain a corresponding alkyne derivative; and d) allowing a copper catalyzed click reaction between the corresponding alkyne derivative as obtained in step b) with an isatin azide under third reaction conditions (temperature range of 20°C-35°C for a period of 25-35 hours) to obtain the compound of Formula II.

Referring now to the drawings, and more particularly to FIGS. 1 through 20, where similar reference characters denote corresponding features consistently throughout the figures, there are shown preferred embodiments.

FIG. 1 illustrates a schematic representation of invention, according to the embodiments as disclosed herein. The invention involves a newly developed process/method in organic chemistry for heterocyclic compounds synthesis and their anticancer and antituberculosis activities. The systematic invention can be described into following modules—

Elements or components or modules of the invention:
A. Discovery of a novel cascade synthesis for fused pyrido-heterocycles
B. Synthesis of substituted 5-azaindoles derivatives
C. Synthesis of substituted γ-carboline derivatives
D. Synthesis of substituted furo[b]pyridines, benzofuropyridine derivatives and furo[b]pyridine-isatin hybrids
E. Evaluation of optical properties
F. In vitro studies against cancer cell lines and multi drug resistant pathogens
G. Anti-mycobacterial properties of novel 5-azaindoles, furopyridines, and their isatin hybrids
H. Experimental procedure or process
Description of the functionality of each module:
1. Brief details about the serendipitous discovery and systematic development of optimized synthetic procedure
2. Substrate scope for invented synthetic methodology and synthesis of 5-azaindole derivatives, mechanistic explanation for synthesis and regioselectivity, rational designing and synthesis of novel CB2 agonist analogue
3. Synthesis of γ-carbolines and BET inhibitor analogue by using newly developed protocol
4. Synthesis of furopyridines and benzofuropyridines
5. Photo-physical studies of novel carbolines: UV absorption and fluorescence studies
6. Cell uptake (confocal microscopy) and cytotoxicity studies on representative carboline derivatives
7. Anti-mycobacterial applications of novel 5-azaindoles and/or furo[b]pyridines and their isatin hybrids Discovery of a novel cascade synthesis for fused pyrido-heterocycles: Azaindoles are exciting heterocyclic motifs due to their wide application in pharmaceutical products. Their structural similarity with interesting biomolecules and limited availability in biological systems make them first choice for modulating natural ligand-protein interactions. The pyrrole glycinates may become a key structural component for developing a range of azaindole core molecules through hetero-annulation strategy. During an attempt of making pyrrole glycinate via imination of N-benzyl pyrrole-2-carboxaldehyde (1a) with glycine methyl ester hydrochloride (2a) in presence of Hünig's base (DIPEA) in refluxing toluene, we found out that the product was not the corresponding imine but later it was characterized to be methyl 1-benzyl-4-(1-benzyl-1H-pyrrol-2-yl)-1H-pyrrolo[3,2-c]pyridine-6-carboxylate (3aa).

The interesting reaction towards an unprecedented synthesis of pyrrolo pyridine (azaindole) was further analyzed to discover the optimal reaction conditions. Various inorganic and organic bases were examined for their efficacy to obtain the desired transformation (Table 1). By systematic variation of equivalents of N-substituted pyrrole 2-aldehyde and base, an appropriate molar ratio to obtain optimal product yield was discovered. Various solvent systems were examined to improve the yield of the desired 5-azaindole.

marized that C-3 nucleophilicity of pyrrole heterocyclic unit plays a crucial role for the heterocyclization.

Figure 3:
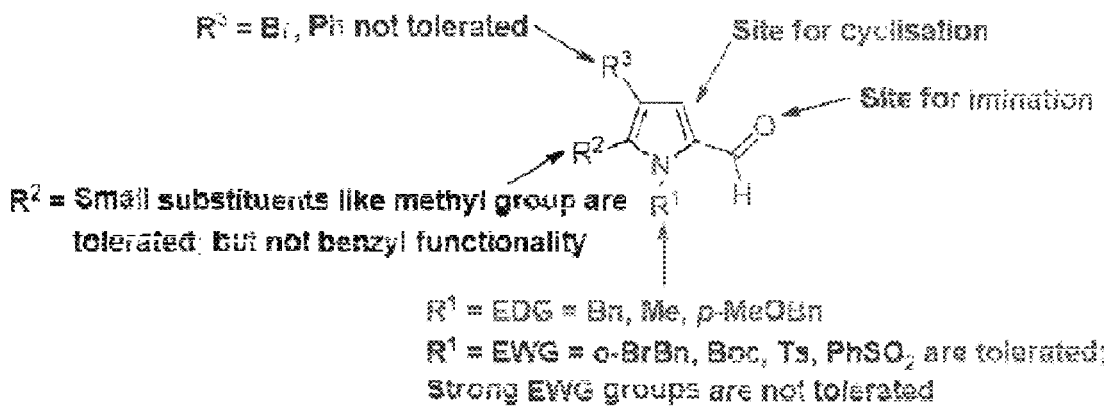
FIG. 3 illustrates an effect of various substituents at 1,4,5-positions of 1-substituted-2-pyrrole aldehydes (1a-i) in the formation of 5-azaindoles 3aa-fa, according to the embodiments as disclosed herein.

FIG. 3 illustrates an effect of various substituents at 1,4,5-positions of 1-substituted-2-pyrrole aldehydes (1a-i) in the formation of 5-azaindoles 3aa-fa, according to the embodiments as disclosed herein. The C-4 substitution on pyrrole subunit is also not tolerated in the methodology, most probably due to steric crowding. Although, sterically less demanding substituents at C-5, for instance methyl group (1f) is well tolerated, bulky substituents at C-5 posi-

TABLE 1

Optimization of reaction conditions for the synthesis of 5-azaindole

Figure 2:
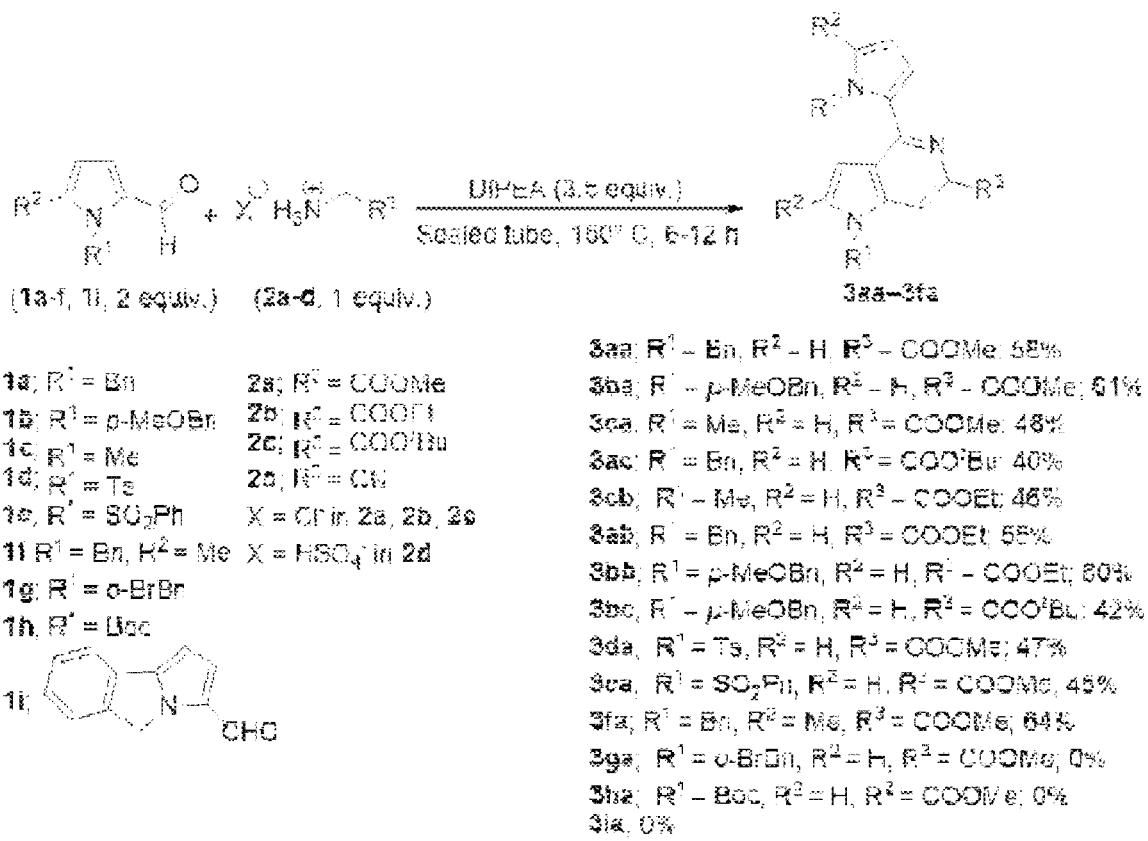
FIG. 2 illustrates synthesis of 5-azaindoles 3aa-fa from N-substituted pyrrole-2-aldehydes 1a-i, according to the embodiments as disclosed herein.

| S. No | Aldehyde (equiv.) | Aminoester HCl (equiv.) | Base (equiv.) | Solvent | Additive | Temperature | Reaction Time | Yield* |
|---|---|---|---|---|---|---|---|---|
| 1. | 1a (1.0) | 2a (1.0) | DIPEA (3.5) | Toluene | 4 Å MS | Reflux | 48 h | 38% (3aa) |
| 2. | 1a (1.0) | 2a (1.0) | Et$_3$N (3.5) | Toluene | 4 Å MS | Reflux | 48 h | NA |
| 3. | 1a (2.0) | 2a (1.0) | K$_2$CO$_3$ (6.5) | Et$_2$O | — | RT to reflux | 24 h | NA |
| 4. | 1a (2.0) | 2a (1.0) | Cs$_2$CO$_3$ (2.0) | DMF | — | RT to reflux | 24 h | NA |
| 5. | 1a (2.0) | 2a (1.0) | NaH (3.5) | THF | — | RT to reflux | 24 h | NA |
| 6. | 1a (2.0) | 2a (1.0) | DBU (3.5) | — | — | 150° C./ Sealed tube | 6 h | 31% (3aa) |
| 7. | 1c (2.0) | 2a (1.0) | DIPEA (3.5) | — | — | 140° C./ 200 mbar (microwave) | 10 min | Trace (3ca) |
| 8. | 1a (2.0) | 2a (1.0) | DIPEA (3.5) | — | — | 50° C./ Sealed tube | 24 h | NA |
| 9. | 1b (2.0) | 2a (1.0) | DIPEA (3.5) | — | — | 80° C./ Sealed tube | 48 h | 43% (3ba) |
| 10. | 1a (1.0) | 2a (5.0) | DIPEA (15.0) | — | — | 100° C./ Sealed tube | 48 h | 34% (3aa) |
| 11. | 1a (2.0) | 2a (1.0) | DIPEA (3.5) | — | DDQ (1.0) | 150° C./ Sealed tube | 16 h | NA |
| 12. | 1a (2.0) | 2a (1.0) | DIPEA (3.5) | — | — | 150° C./ Sealed tube | 6 h | 58% (3aa) | equiv. = no. of equivalents;
NA = not applicable;
*isolated yield of pure compounds FIG. 2 illustrates synthesis of 5-azaindoles 3aa-fa from N-substituted pyrrole-2-aldehydes 1a-i, according to the embodiments as disclosed herein. A number of reaction conditions were tested including neat reaction and microwave irradiation. With a series of experimental data in our hand, we concluded that a mixture of 2.0 equivalents of N-benzylpyrrole-2-carboxaldehyde (1a) and 1.0 equivalent of glycine alkyl ester hydrochloride in the presence of 3.5 equivalents of DIPEA, upon heating in a sealed tube at 150° C. afforded the optimum yield of 58% of desired 5-azaindole (3aa) via the newly discovered reaction (as shown in FIG. 2).

Synthesis of substituted 5-azaindoles derivatives: Further, a series of N-substituted pyrrole-2-aldehydes (1b-j) were reacted to observe that the azaindole transformation takes place smoothly when electron rich N-substituents are available on pyrrole-2-carboxaldehyde subunit viz., 4-methoxybenzyl (1b), methyl (1c) functional groups. The pyrrole-2-carboxaldehyde derivatives with mild electron withdrawing groups such as tosyl (1d) and phenylsulfonyl (1e) underwent similar heterocyclization reaction to afford corresponding azaindole derivatives, however with longer reaction time and moderate yields. When N-Bocpyrrole-2-carboxaldehyde (1h) or 5H-pyrrolo[2,1-a]isoindole-3-carbaldehyde (1i) was subjected under similar reaction conditions, no traces of the resultant azaindole products were formed, due to strong electron withdrawing tendency of Boc protecting group in 1h and highly strained pyrrolefused isoindole ring system in 1i. Overall with these results in hand, we sumtion of pyrrole unit, like benzyl group resulted in no formation of the 5-azaindole product even after heating at 150° C. for 48 h.

Figure 4:
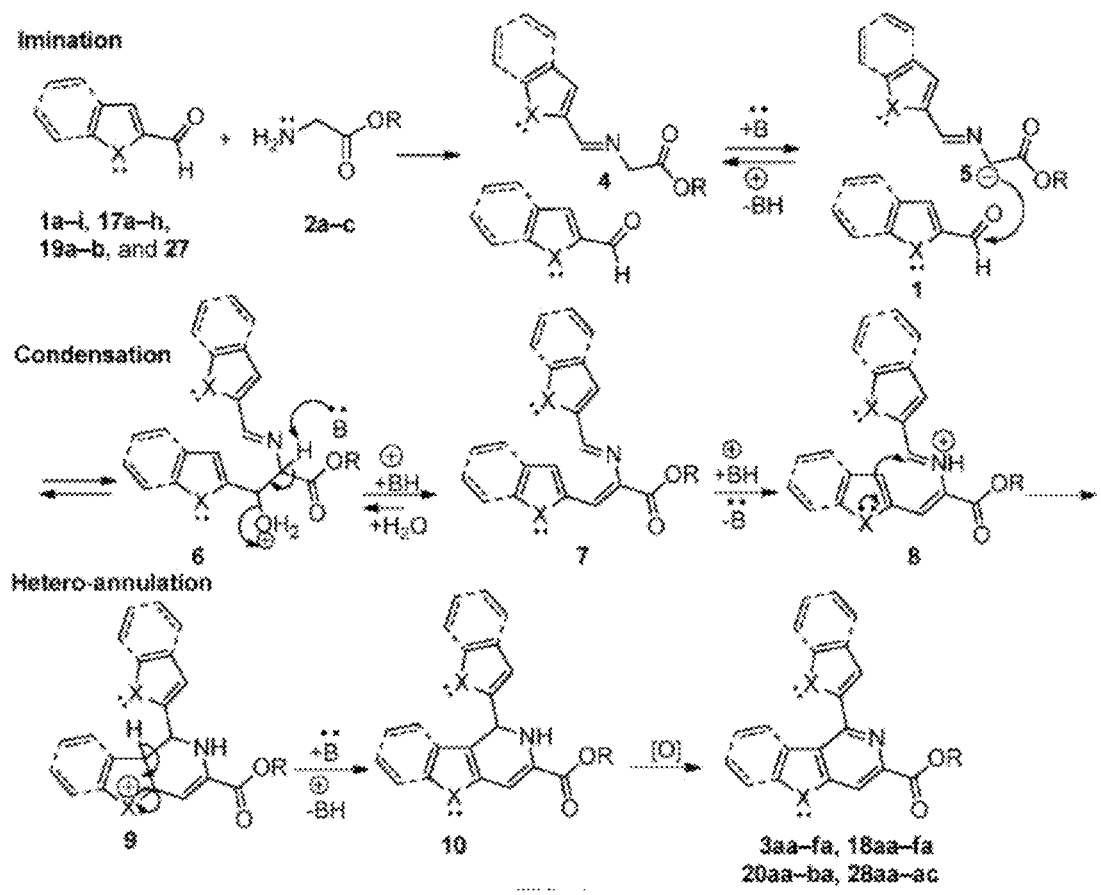
FIG. 4 illustrates a plausible mechanism for the formation of 5-azaindoles (3aa-fa), carbolines (18aa-fa) and azabenzofurans (20aa-ba), and pyridobenzofurans (28aa-ac), according to the embodiments as disclosed herein.

FIG. 4 illustrates a plausible mechanism for the formation of 5-azaindoles (3aa-fa), carbolines (18aa-fa) and Azabenzofurans (20aa-ba), and pyridobenzofurans (28aa-ac), according to the embodiments as disclosed herein. The probable mechanism (as shown in FIG. 4) for the conversion of the various heterocyclo or benzofused heterocyclo 2-aldehydes (1a-i, 17a-h, 19a-b, and 27) to corresponding fused pyrido heterocycles (3aa-fa, 18aa-fa, 20aa-ba, and 28aa-ac) involves initial formation of trans imine 4 from heterocyclic 2-aldehydes and glycine alkyl esters (2a-c). In the presence of Hunig's base, iminonucleophile 5 is generated by abstraction of active methylene proton from trans-imine 4 which further undergoes nucleophilic addition reaction with another molecule of heterocyclic-2-aldehydes (1a-i, 17a-h, 19a-b, and 27) to give an intermediate imino alcohol 6. Imino alcohol 6 eliminates a molecule of water under the reaction conditions to give iminoenamine intermediate 7. The imine double bond in the intermediate 7 is activated by the conjugate acid (+BH) for electrophilic aromatic substitution at 3-position of heterocyclic unit to form the second C—C bond through iminium intermediate 8 which aromatizes by loss of proton to give intermediate 10. In situ dehydrogenation of 10 by autoxidation leads to the formation of desired fused pyrido-compounds (3aa-fa, 18aa-fa, 20aa-ba, and 28aa-ac).

Figure 5:
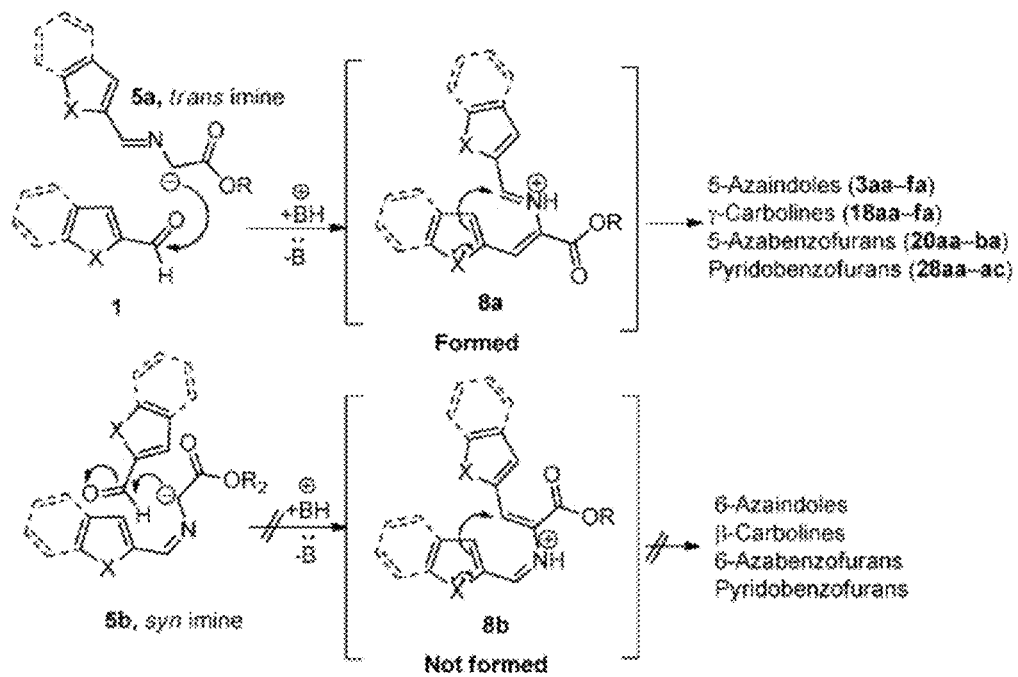
FIG. 5 illustrates an explanation for the formation of 5-regiosmers of various heterocycles instead of 6-regioisomers, according to the embodiments as disclosed herein.

FIG. 5 illustrates an explanation for the formation of 5-regiosmers of various heterocycles instead of 6-regioisomers, according to the embodiments as disclosed herein. The exclusive formation of 5-regio-isomer is explained by invoking the participation of trans imine nucleophile 5a in the first C—C bond formation via nucleophilic addition to heterecyclic-2-carbaldehyde 1 to give 5-regioisomer intermediate 8a, whereas the formation of 6-regioisomer intermediate 8b is disfavored due to steric crowding between the reaction of nucleophile derived from syn imine 5b and heterocyclic-2-carbaldehyde 1 (as shown in FIG. 5). The iminium intermediate 8a undergoes nucleophilic substitution at 3-position of heterocyclic or benzofused aldehyde to form the second C—C bond formation resulting in the ring closure via heterocyclization to give dihydro intermediate 9 which on aromatization and autooxidation afford the various heterocycles such as 5-azaindoles, γ-carbolines, 5-azabenzofurans and pyridobenzofurans.

Figure 6:
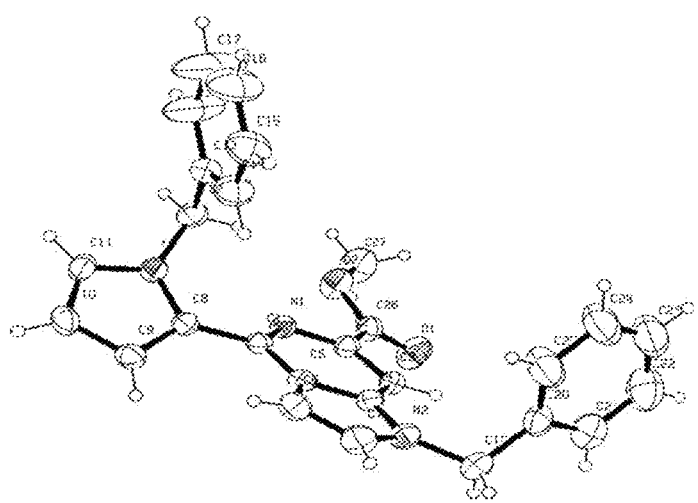
FIG. 6 illustrates single crystal XRD analysis for 5-azaindole derivative 3aa (CCDC 1836867), according to the embodiments as disclosed herein.

FIG. 6 illustrates single crystal XRD analysis for 5-azaindole derivative 3aa (CCDC 1836867), according to the embodiments as disclosed herein. Further, the ester 3aa was reacted with aqueous ammonia in alkaline methanolic solution to yield corresponding amide derivative 11. Mild dehydration of 11 in phosphoryl chloride provided cyano-azaindole 12. The ester 3aa quickly reacts with lithium aluminium hydride to give corresponding alcohol 13.

Figure 7:
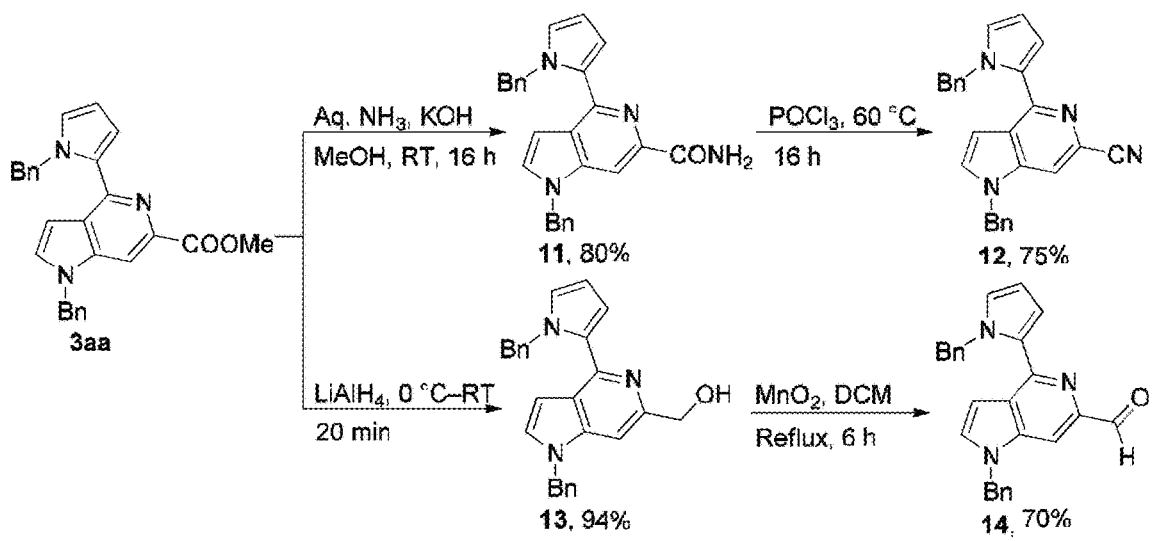
FIG. 7 illustrates synthesis of novel 5-azaindole derivatives (11-14), according to the embodiments as disclosed herein.

FIG. 7 illustrates synthesis of novel 5-azaindole derivatives (11-14), according to the embodiments as disclosed herein. Introducing formyl moiety in azaindoles at six membered ring, sparing the highly nucleophilic C-3 and C-2 position of indole can also be achieved through this methodology as the alcohol 13 can readily be oxidised into aldehyde 14 by a treatment of manganese dioxide in refluxing dichloromethane (as shown in FIG. 7).

Figure 8:
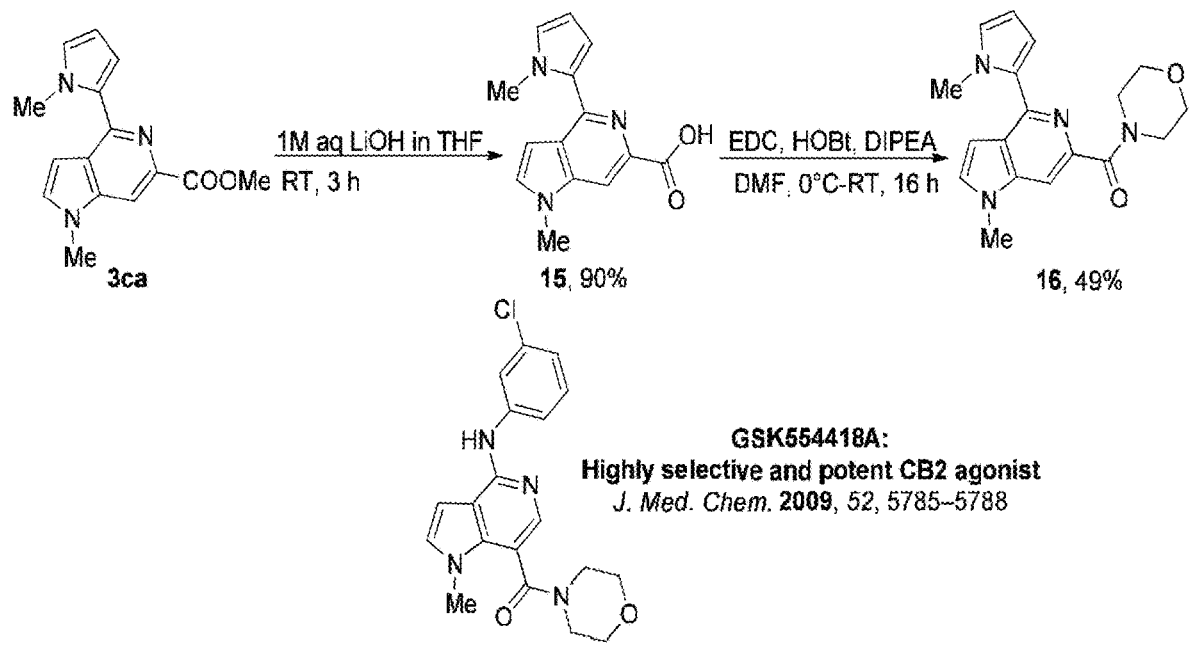
FIG. 8 illustrates synthesis of proposed CB2 agonist (16), according to the embodiments as disclosed herein.

FIG. 8 illustrates synthesis of proposed CB2 agonist (16), according to the embodiments as disclosed herein. Cannabinoid receptors are trans-membrane proteins belonging to G-protein coupled receptor superfamily. These receptors are of two types namely, CB1 and CB2. The cannabinoid-cannabinoid receptor interaction is well studied for their antipalliative effects and CB2 receptor has been selectively targeted for the treatment of neuropathic pain. Contemporary literature shows that CB2 can become a vital target for developing new anticancer molecules as CB2 agonists can regulate key cell signaling pathways including cell survival, angiogenesis, and metastasis. It was envisaged that the compound 3ca have remarkable structural similarity with selective CB2 agonist GSK554418A reported in the literature and expected to exhibit similar biological activity. Therefore, methyl ester of 3ca was hydrolysed into corresponding 5-azaindole acid (15). Thereafter, 15 was coupled with morpholine to give 16 (as shown in FIG. 8). The in vitro studies to confirm CB2 agonistic activity of 3ca and 16 in cancer cell lines are ongoing in our laboratory.

FIG. 9 illustrate synthesis of γ-carbolines 18aa-fa, according to the embodiments as disclosed herein. Carbolines are Bromodomain and extra terminal (BET) proteins have emerged as a novel class of therapeutic targets for treating cancer. There are 46 bromodomain-containing proteins encoded in the human genome and largely they are classified into eight subfamilies. Existing studies suggest that careful regulation of gene transcription by selective targeting of bromodomains may bring innovative changes in the way we treat cancer. BET inhibitors are rapidly advancing into clinical trials for various human cancers for instance, IBET-762 (sponsor-GSK, for treatment of carcinoma, currently in clinical trial phase 1) and OTX015 (sponsor-Oncoethix, for treatment of leukemia, currently in clinical trial phase 1). Recently, some synthetic γ-carboline derivatives have shown selective bromodomain inhibition at low nanomolar concentrations.

Synthesis of substituted γ-carboline derivatives: As depicted in the proposed mechanism (as shown in FIG. 4), it was envisioned that a library of fused-pyrido heterocycles can be prepared by the process of the present invention. To check our hypothesis, we prepared a series of N-substituted indole-2-carboxaldehyde derivatives (17a-h) using standard reactions. N-methyl indole-2-carboxaldehyde (2 equiv.) and glycine methyl ester hydrochloride (2a-c, 1 equiv.) were heated with DIPEA (3.5 equiv.) at 120° C. in a sealed tube for 3-9 h to give corresponding γ-carboline derivative (18aa-fa, Scheme 6). Remarkably, the N-protected indole-2-carboxaldehyde derivatives were found to be more reactive than contemporary N-substituted pyrrole-2-carboxaldehyde derivative (1a-i) in the standard reaction conditions of the protocol.

FIG. 10 illustrates Single crystal XRD analysis for γ-carboline derivative 18ac (CCDC: 1897787), according to the embodiments as disclosed herein.

Figure 11:
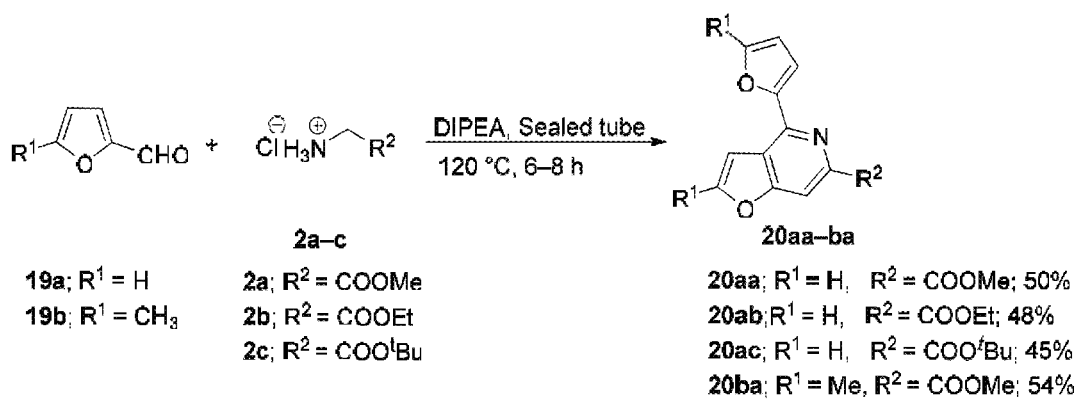
FIG. 11 illustrates synthesis of furo[b]pyridines (20aa-ba), according to the embodiments as disclosed herein.

FIG. 11 illustrates synthesis of furo[b]pyridines (20aa-ba), according to the embodiments as disclosed herein. Synthesis of substituted furo[b]pyridines, benzofuropyridine derivatives and furo[b]pyridine-isatin hybrid: Furfural (19a) and 5-methyl furfural (19b) were subjected to standard reaction conditions developed in our laboratory, and these substrates were successfully transformed into their corresponding furo[b]pyridines (20aa-ba). The synthesized derivatives of this class of compounds have been discovered to exhibit anti-tuberculosis properties in Mycobacterium strains that causes tuberculosis. Moreover, furo[b]pyridine-isatin hybrid molecule (26) has been synthesized to further improve the efficacy for antituberculosis activities.

Figure 12:
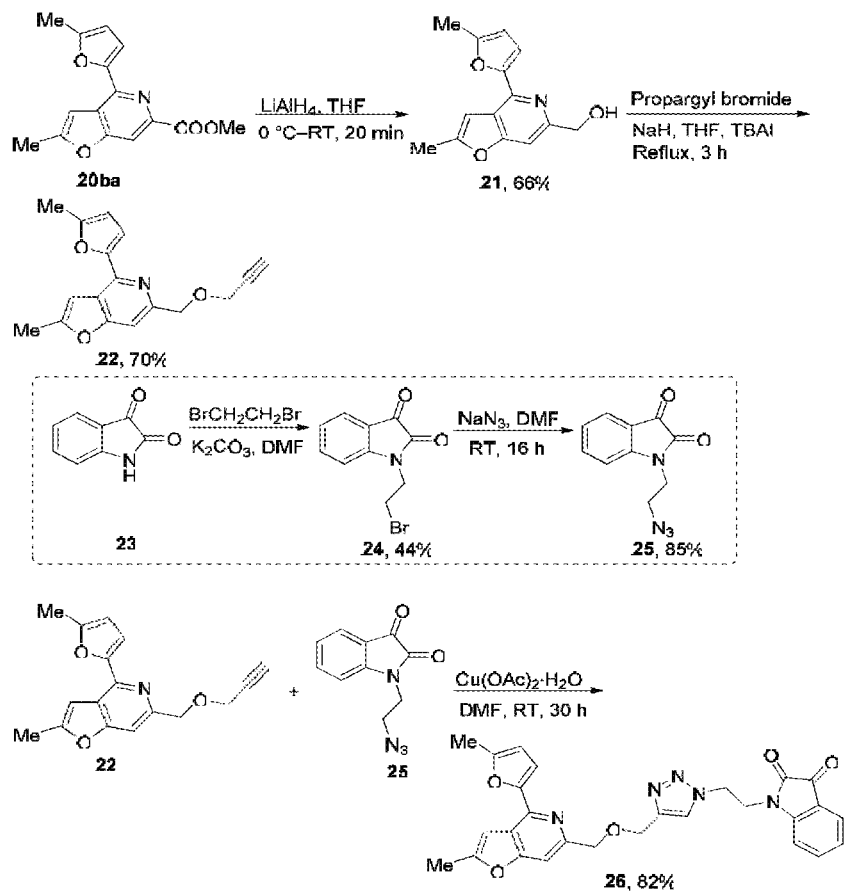
FIG. 12 illustrates synthesis of furopyridine-isatin hybrid (26) for antituberculosis activity, according to the embodiments as disclosed herein.

FIG. 12 illustrates synthesis of furopyridine-isatin hybrid (26) for antituberculosis activity, according to the embodiments as disclosed herein. Initial assessment of novel furo[b]pyridines was found to be very promising. The furo[b]pyridine 20ba was treated with LiAlH4 to get corresponding alcohol 21. The propargylation of this alcohol afforded alkyne derivative 22 and the synthesis of isatin-azide 25 was performed according to the literature report. The click chemistry between 22 and 25 smoothly transformed into novel furopyridine-isatin hybrid 26 (as shown in FIG. 10). The anti-mycobacterial screening of all the furopyridine derivatives along with isatin hybrid in multidrug and extensive drug resistant (MDR) strains of Mycobacterium tuberculosis, and anti-biofilm activity against a panel of biofilm forming bacteria or pathogens were carried out and found to possess interesting antituberculosis activities.

Figure 13:
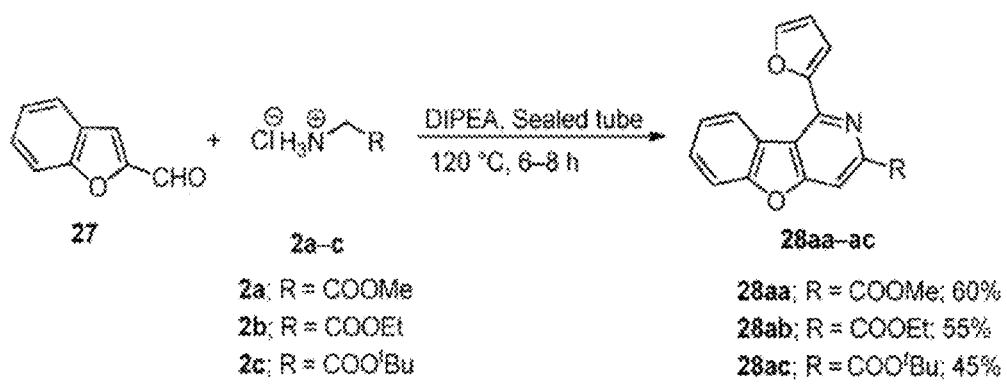
FIG. 13 illustrates synthesis of benzofuropyridines (28aa-ac), according to the embodiments as disclosed herein.

FIG. 13 illustrates synthesis of benzofuropyridines (28aa-ac), according to the embodiments as disclosed herein. The versatility of the discovered methodology was again established by the reaction of benzofuran-2-carboxaldehyde 27 with glycine alkyl esters (2a-c) to obtain novel benzofuro fused pyridine derivatives (28aa-ac) as shown in the FIG. 11. All the heterocycles synthesized by the present method, are the only identifiable products of their respective reactions.

Figure 14:
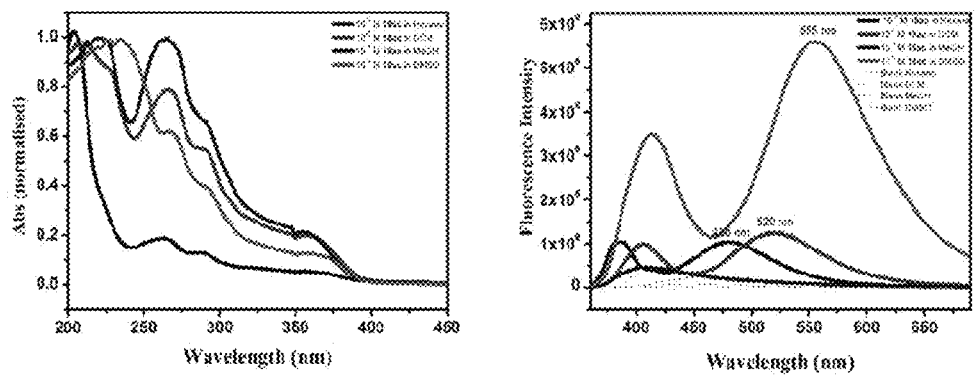
FIG. 14 illustrates synthesis of benzofuropyridines (28aa-ac), according to the embodiments as disclosed herein.

FIG. 14 illustrates synthesis of benzofuropyridines (28aa-ac), according to the embodiments as disclosed herein. Evaluation of optical properties: Photophysical properties were studied for one of the synthesized carboline derivatives 18ac. 10-5 M solutions of 18ac were prepared in four different organic solvents namely dichloromethane ($CH_2Cl_2$), methanol (MeOH), dimethylsulfoxide (DMSO), and n-hexane. It was observed that UV absorption features for compound 18ac does not rely much on the solvent polarity. The absorption maxima ($\lambda$max) was observed at 230 nm for 18ac in DMSO. Later, fluorescence studies were carried out for 18ac using same four solutions, and a bathochromic shift of almost 40 nm was observed upon changing the solvent from non-polar hexane to moderately polar dichloromethane and then highly polar DMSO (Table 2; FIG. 14). The innate fluorescence of 18ac was found to be quenched in polar-protic solvent methanol which can be attributed to the ultrafast solute-solvent intermolecular photo-induced electron transfer facilitated by hydrogen bonding interactions in highly polar solvents.

TABLE 2

Measurement of absorptivity ($\varepsilon$) and half-life ($\tau$) of 18ac

| Solvent | $\lambda_{abs}$ (nm) | $\varepsilon$ ($10^3$ M$^{-1}$ cm$^{-1}$) | $\lambda_{em}$ (nm) | $\tau$ (ns) |
|---|---|---|---|---|
| Hexane | 204, 262, 290, 355 | 0.78 | 386, 480 | 1.90 |
| DCM | 210, 266, 290, 356 | 1.01 | 405, 520 | 4.73 |
| MeOH | 220, 265, 290, 355 | 2.05 | 407, 422 | 0.99 |
| DMSO | 230, 266, 290, 357 | 1.67 | 413, 555 | 8.35 |

Figure 15:
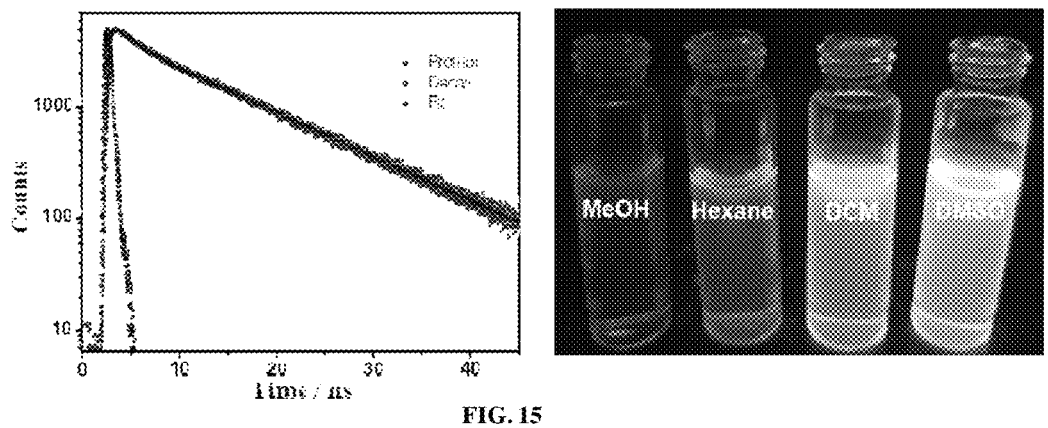
FIG. 15 illustrates Fluorescence decay profile of 18ac in DMSO (left side; λexc 360 nm) and 10-5 M solutions of compound 18ac in four different solvents under UV chamber (right side), according to the embodiments as disclosed herein.

FIG. 15 illustrates Fluorescence decay profile of 18ac in DMSO (left side; $\lambda$exc 360 nm) and 10-5 M solutions of compound 18ac in four different solvents under UV chamber (right side), according to the embodiments as disclosed herein. Fluorescence life-times were measured by time-correlated single-photon counting (TCSPC) experiment. Generally, longer fluorescence life times are correlated with higher quantum yields and good imaging contrast. Organic molecules are ideal choice for FRET studies as they are classified under "rigid dyes". Delightfully, 18ac was found to be highly fluorescent in DMSO and DCM with an average fluorescence life-time of 8.35 nanoseconds (ns) and 4.73 ns, respectively (Table 2; FIG. 15).

Figure 16:
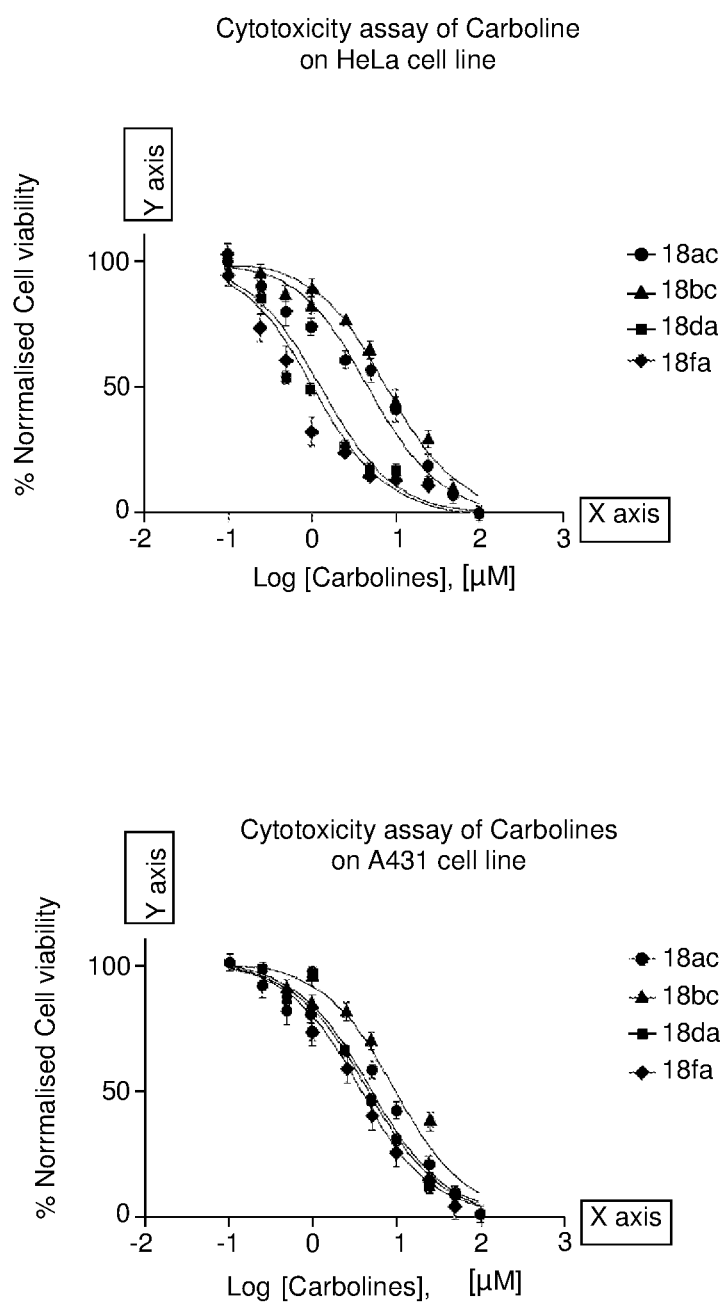
FIG. 16 illustrates Dose vs Response curves of carbolines 18ac, 18bc, 18da and 18fa in human cancer cell lines HeLa, MCF-7, HEK293, A431 and A549. IC50 value was determined by standard crystal violet assay in triplicate, according to the embodiments as disclosed herein.
Figure 16:
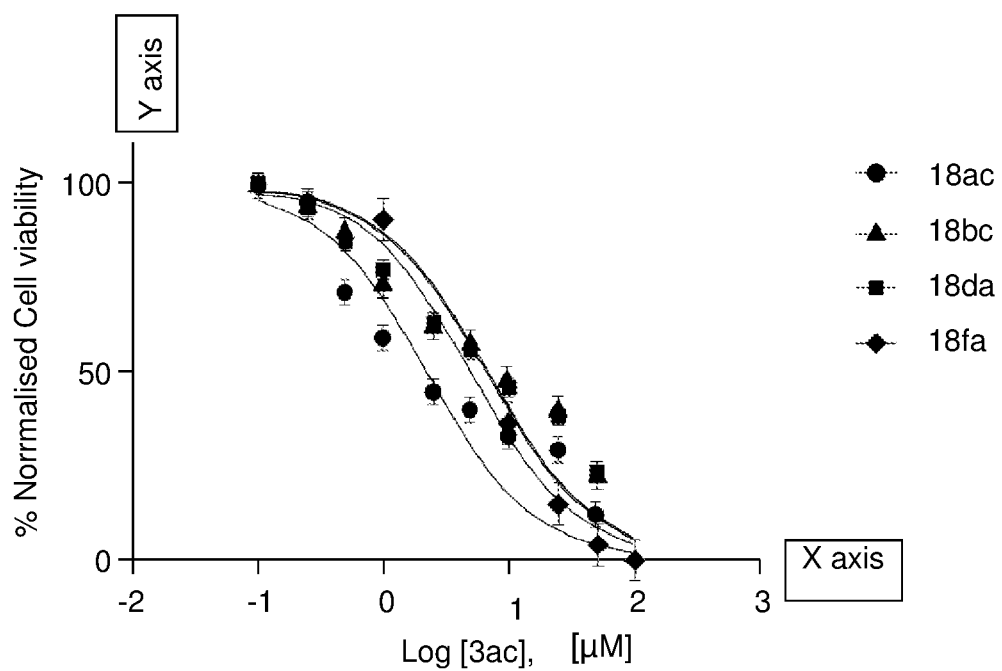

FIG. 16 illustrates dose vs response curves of carbolines 18ac, 18bc, 18da and 18fa in HeLa, MCF-7, HEK293, A431 and A549 cell lines for 48 h incubation. IC$_{50}$ values were determined by standard crystal violet assay in triplicate, according to the embodiments as disclosed herein. In vitro studies: The cytotoxicity of novel carboline derivatives 18ac, 18bc, 18da and 18fa were tested through standard crystal violet assay on human malignant cell lines such as HeLa, MCF-7, HEK293, A431 and A549. Cells were plated in a 96 well plate (1800 cells per well) and incubated for 48 h at 37° C. under 5% CO$_2$. At 50% confluency, cells were incubated with a series of concentrations (0.1 µM, 0.25 µM, 0.5 µM, 1 µM, 2.5 µM, 5 µM, 10 µM, 25 µM, 50 µM and 100 µM) of the carbolines 18ac, 18bc, 18da and 18fa, respectively, for 48 h. The results (Table 3) of these assays revealed that carbolines were cytotoxic in micro molar concentrations.

TABLE 3

IC$_{50}$ study of carbolines 18a, 18bc, 18da, and 18fa in HeLa, MCF7, HEK 293, A431 and A549 cell lines as DNA intercalators (48 h incubation)

| Carbolines | HeLa (IC$_{50}$) | MCF7 (IC$_{50}$) | HEK293 (IC$_{50}$) | A431 (IC$_{50}$) | A549 (IC$_{50}$) |
|---|---|---|---|---|---|
| 18ac | 4.89 µM | 5.59 µM | 2.29 µM | 4.89 µM | 4.62 µM |
| 18bc | 8.15 µM | 7.07 µM | 7.14 µM | 9.18 µM | 5.47 µM |
| 18da | 1.30 µM | 2.99 µM | 6.73 µM | 4.47 µM | 5.17 µM |
| 18fa | 1.07 µM | 3.71 µM | 4.98 µM | 3.576 µM | 4.98 µM |

Figure 17:
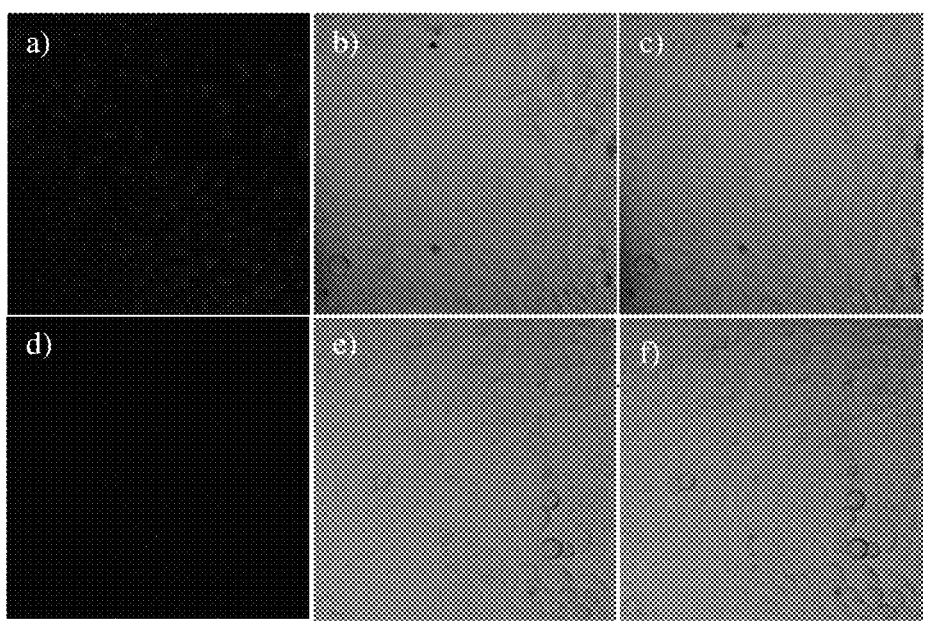
FIG. 17 illustrates confocal microscopic studies (λex=405 nm; collection range=420-470 nm) for uptake of 18ac in HeLa cells, according to the embodiments as disclosed herein.

FIG. 17 illustrates confocal microscopic studies ($\lambda$ex=405 nm; collection range=420-470 nm) for uptake of 18ac in HeLa cells, according to the embodiments as disclosed herein.
a) Confocal fluorescent image of HeLa cells after 3 h incubation with 10 µM concentration of 18ac (20× magnification, 2× zoom);
b) DIC image of HeLa cells
c) Overlay of (a) and (b)
d) Confocal image of HeLa cells after 3 h incubation with 100 nM concentration of 18ac (20× magnification, 2× zoom)
e) DIC image of HeLa cells
f) Overlay of (d) and (e).

To further evaluate cell uptake of the novel carbolines, live-cell imaging experiment was performed. HeLa cells were plated in a 4-well confocal dish (cell count=104 cells per well) and incubated for 48 h at 37° C. under 5% CO2. After 3 h of incubation with 18ac (10 nM, 100 nM, 1 µM, 10 µM, and 100 µM), cellular uptake and distribution were monitored by using confocal microscopy ($\lambda$ex=405 nm; collection range=420-470 nm). Decent cytosolic uptake of 18ac was observed in cancer cells while incubating with 10 µM concentration, whereas nominal uptake was observed with 100 nM concentration.

Figure 18:
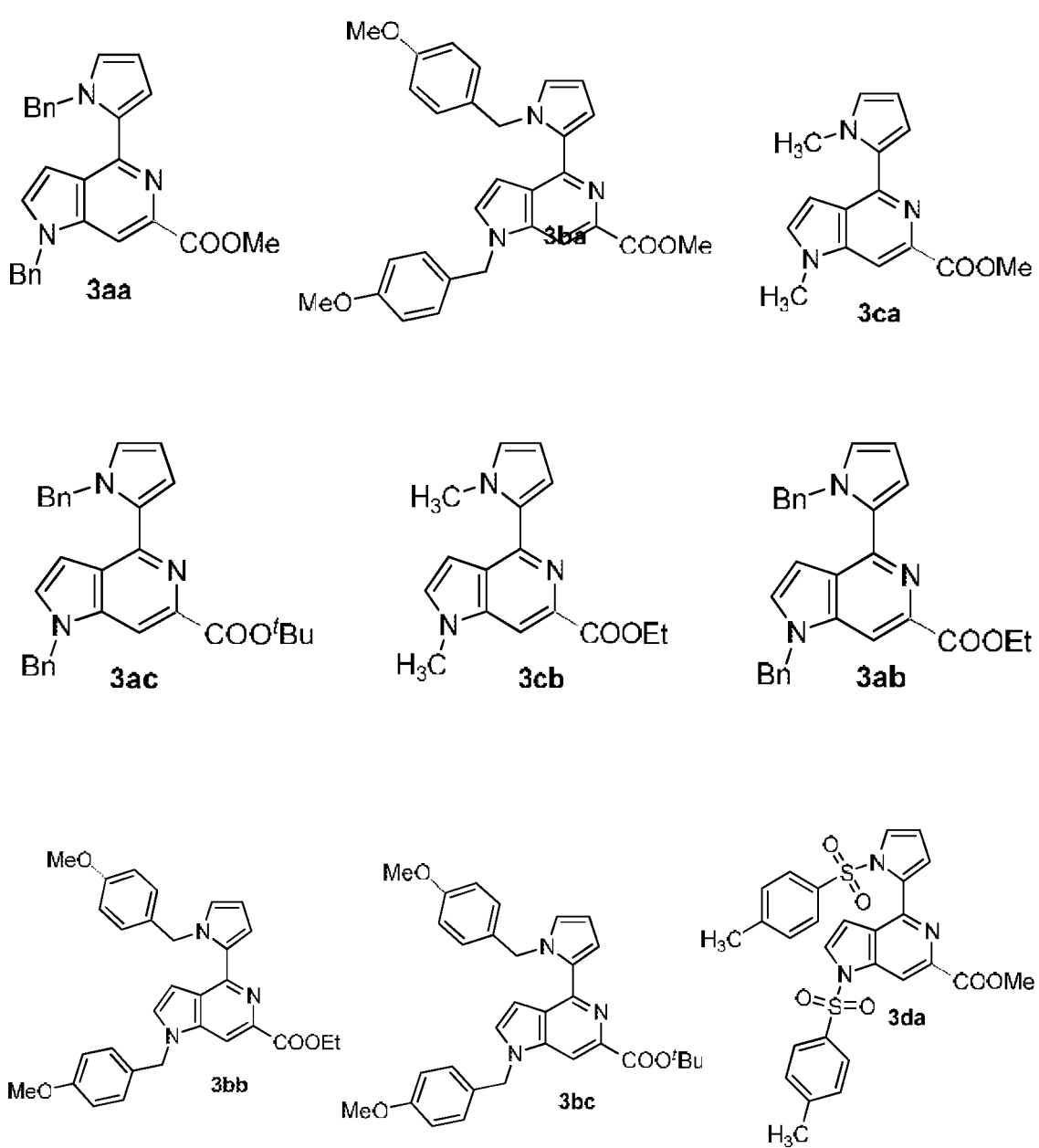
FIG. 18 illustrates structural formula of various chemical compounds, according to the embodiments as disclosed herein.
Figure 18:
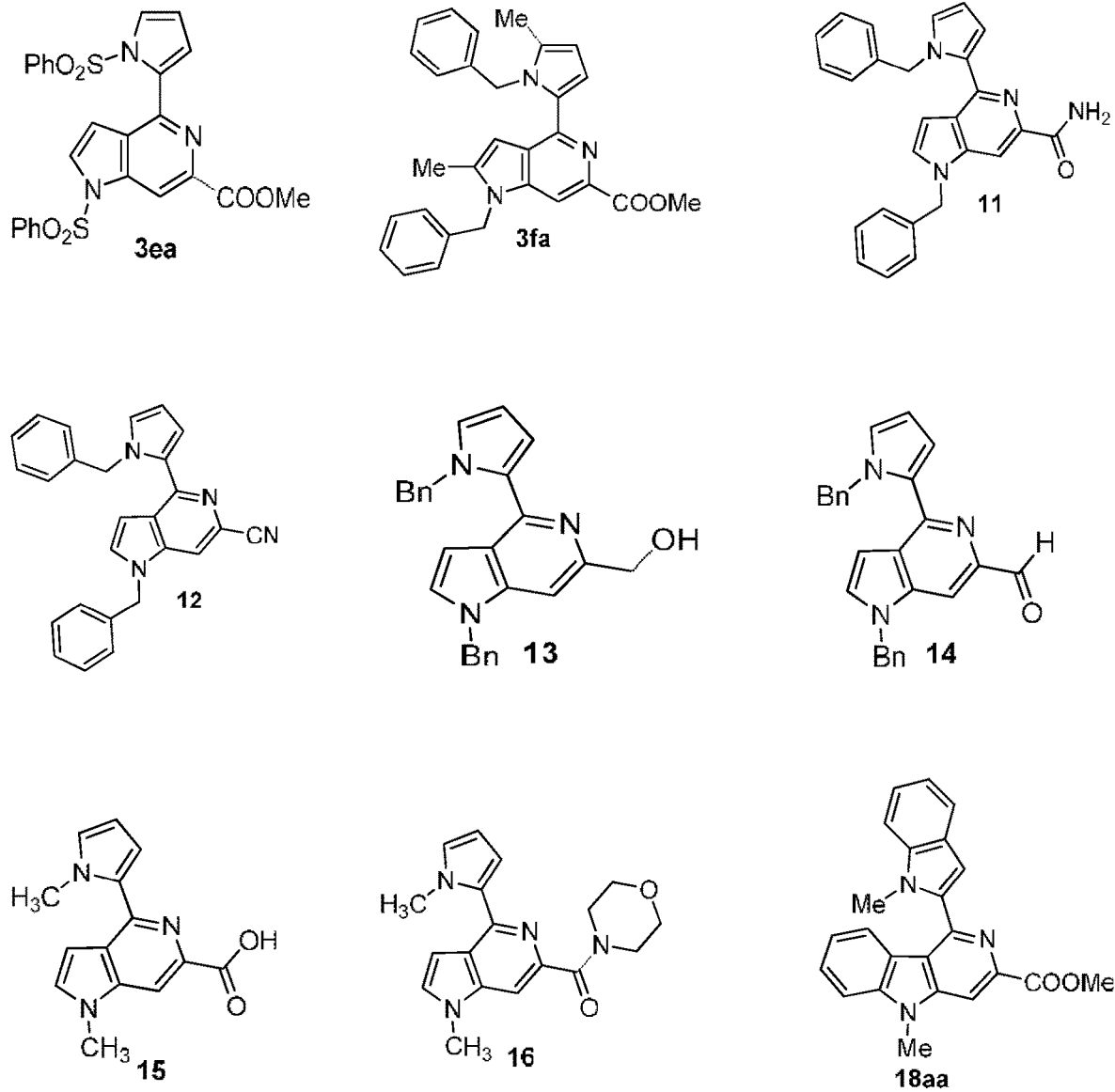

FIG. 18 illustrates structural formula of various chemical compounds, according to the embodiments as disclosed herein.

FIG. 19 illustrates key features of the invention that differentiates the invention from existing protocols, according to the embodiments as disclosed herein.

In vitro anti-mycobacterial activities of novel furo[b]pyridines and their isatin hybrids against non-virulent (Mycobacterium smegmatis) and virulent/opportunistic mycobacterium strains (Mycobacterium bovis)

The newly synthesized furo[b]pyridine isatin hybrid derivative 26 (also labelled as, CV-PD-PF-IST-HBD-001, was tested against non-virulent (Mycobacterium smegmatis) and BCG virulent (Mycobacterium bovis) multidrug resistant strains and the results are shown in FIG. 20. It has been observed that the furo[b]pyridine-isatin hybrid drug 26 was active in a concentration range of 70-100 µM for an incubation period of 24 hrs and 48 hrs in non-virulent and virulent multidrug resistant mycobacterium strains, respectively. The results are exciting and potentiate a modification or alteration in the drug design to develop new antituberculosis drugs from India for ending millions of deaths occurring across the developing countries.

FIG. 20 illustrates in vitro antituberculosis activity of furo[b]pyridine-isatin hybrid derivative 26 against Mycobacterium smegmatis (50-100 µM); SD (n=3) and multidrug resistant/opportunistic Mycobacterium bovis (70-100 µM); SD (n=3), according to the embodiments as disclosed herein.

Experimental Procedures:

Procedure for cytotoxicity assay of carbolines in cancer cell lines: For this purpose, carbolines 18ac, 18bc, 18da and 18fa were subjected to a standard cell viability study (Crystal Violet assay) for examining anticancer activity against various human cancer cell lines such as HeLa, MCF-7, HEK293, A431 and A549. Crystal Violet is a triarylmethane dye which stains adhered cells by binding to the ribose moiety in DNA. The amount of Crystal Violet stain in the assay is directly proportional to the live cell biomass adhered on the plate after repeated washing. The above human cancer cell lines were plated in a 96-well tissue culture plate (1800 cells/well,) and incubated for 48 h in RPMI 1640 medium (volume≥100 µL/well), supplemented with 10% heat inactivated fetal bovine serum (HIFBS) and 1% Penicillin-Streptomycin antibiotic at 37° C., 5% CO2. Once the monolayer achieved 50% confluency/well, spent medium was aspirated and replaced with fresh medium≥100 µL/well, supplemented with increasing concentrations of carbolines 18ac, 18bc, 18da and 18fa (0.1 µM, 0.25 µM, 0.5 µM, 1 µM, 2.5 µM, 5 µM, 10 µM, 25 µM, 50 µM and 100 µM), respectively, and incubated for 48 h, at 37° C., 5% CO2. For positive control, 40% DMSO in culture medium was added to three wells and incubated under identical conditions. Cells were treated in triplicate for each concentration. The medium/well was aspirated after 48 h, the cells were washed twice under a gentle stream of tap water and the plate was inverted on filter paper to remove remaining liquid. For measuring cell viability, 50 µL of 0.5% Crystal Violet staining solution (0.5 g crystal violet powder, 80 mL distilled H2O 20 mL methanol) was added to each well and incubated for 20 minutes, at room temperature on a bench rocker (~frequency of 20 oscillations/minute). The plate was again washed gently as described previously, and left to air-dry for 2 h, at room temperature. The Crystal Violet dye was then solubilized by adding 200 µL methanol/well and the plate incubated for 20 minutes, at room temperature. Finally, optical density of each well was measured at 570 nm (OD570) using Synergy H1 multimode plate reader (BioTek Instruments, Inc., Winooski, Vt., USA). The average background OD570 of empty wells was measured and subtracted from OD570/well on the plate. The percentage of treated, viable cells (attached) was determined and a dose vs response curve was plotted as semi-log[conc] vs percentage of normalized cell viability using GraphPad Prism v. 6.02 (GraphPad Software, San Diego, Calif.). The half maximal inhibitory concentration (IC50) was calculated and shown in Table 3 for carbolines 18ac, 18bc, 18da and 18fa against various human cancer cell lines (FIG. 16).

FIG. 17 illustrates confocal microscopic studies ($\lambda$ex=405 nm; collection range=420-470 nm) for uptake of 18ac in HeLa cells, according to the embodiments as disclosed herein.

FIG. 18 illustrates structural formula of various chemical compounds, according to the embodiments as disclosed herein.

FIG. 19 illustrates key features of the invention that differentiates the invention from existing protocols, according to the embodiments as disclosed herein.

Procedure for bacterial culture preparation and in vitro killing assay of *Mycobacterium* strains Bacterial Culture Preparation
  i. Single colony of *Mycobacterium smegmatis* (*M.smeg*) or *Mycobacterium bovis* (BCG) inoculated in 7H9 Middlebrook media containing Tween80
  ii. Bacterial culture grown at 37° C. for 36-48 h
  iii. 1 mL of grown *Mycobacterium smegmatis* or *Mycobacterium bovis* (BCG) is centrifuged at 5000 rpm for 5 min at room temperature (RT).
  iv. Supernatant is discarded and the pellet is dissolved in 1 ml of autoclaved 1× PBS.
  v. Again the culture is spin at 5000 rpm for 5 min at RT
  vi. Pellet formed here is then dissolved in 1× PBS for further experiments In Vitro *Mycobacterium* Strains Killing Assay
  a. $OD_{600}$ of *Mycobacterium smegmatis* or *Mycobacterium bovis* is measured and set to 0.1
  b. Mixture of bacteria and different drug concentrations (5-azaindoles or furo[b]pyridines or furo[b]pyridine-isatin hybrids) is prepared individually in microcentrifuge tubes (maintaining 200 µL as volume of the mixture for all concentrations)
  c. Tubes containing the bacteria and drug mixtures are incubated at 37° C. for 0, 6, 12, 24 hours
  d. After every individual time point, 1:10 serial dilutions up to $10^{-5}$ are prepared (using 1× PBST) for each set containing all concentrations
  e. Plating of $10^{-3}$, $10^{-4}$, $10^{-5}$ (5 µL spots) are put in petri dish containing 7H9/LB agar media
  f. Plates are incubated at 37° C. for 36 h or more for visible bacterial colonies to appear
  g. Colony counting is performed using a colony counter FIG. 20 illustrates in vitro antituberculosis activity of furo[b]pyridine-isatin hybrid derivative 26 against *Mycobacterium smegmatis* (50-100 µM); SD (n=3) and multidrug resistant/opportunistic *Mycobacterium bovis* (70-100 µM); SD (n=3), according to the embodiments as disclosed herein.

EXAMPLES

Example 1

General procedure for the synthesis of fused pyrido heterocycles (3aa-fa, 18aa-fa, 20aa-ba, and 28aa-ac). A mixture of aldehyde (1a-i, 17a-h, 19a-b, or 27, 2.00 mmol), glycine alkyl ester hydrochloride (2a-c, 1.00 mmol), and N,N-Diisopropylethylamine (DIPEA, 3.50 mmol) was heated at 120-150° C. for 3-12 h in a sealed tube (25 mL, Borosilicate) with constant stirring (monitored by TLC). The reaction mixture was cooled to room temperature, diluted with $CH_2Cl_2$ (1×10 mL) and washed with brine (1×10 mL). The reaction mixture was further extracted with $CH_2Cl_2$ (3×10 mL). The combined organic layer was dried over anhydrous $Na_2SO_4$, filtered, concentrated, and purified over neutral alumina (175 mesh) column chromatography using hexane-EtOAc solvent mixture as eluent.

Example 2

Methyl1-benzyl-4-(1-benzyl-1H-pyrrol-2-yl)-1H-pyrrolo[3,2-c]pyridine-6-carboxylate (3aa). According to the general procedure mentioned above, 1a (100 mg, 0.54 mmol), 2a (34 mg, 0.27 mmol) and DIPEA (0.165 mL, 0.95 mmol) were heated in a sealed tube at 150° C. for 6 h. After workup, the crude residue was purified through alumina (neutral, 175 mesh) column chromatography using hexane-EtOAc (94:6) as eluent; Yield 58% (66 mg); Yellow crystalline solid; m.p.=134-136° C.; Rf 0.65 (2:1 hexane-EtOAc); IR (KBr) 3028 (=C—H), 2922-2850 (C—H), 1722 (C=O), 1712-1554 (C=C), 1357 (C—H bend), 779 (=C—H bend) cm-1; 1H NMR (500 MHz, CDCl$_3$) δ 8.01 (s, 1H), 7.35-7.27 (m, 3H), 7.24 (d, J=3.2 Hz, 1H), 7.18-7.13 (m, 2H), 7.12-7.08 (m, 3H), 7.07-7.02 (m, 2H), 6.91 (d, J=3.2 Hz, 1H), 6.90-6.87 (m, 1H), 6.82 (dd, J=3.7, 1.7 Hz, 1H), 6.29 (dd, J=2.9, 2.3 Hz, 1H), 5.88 (s, 2H), 5.34 (s, 2H), 3.95 (s, 3H); $^{13}$C NMR (100 MHz, CDCl$_3$) δ 167.4, 145.8, 140.5, 139.6, 138.7, 136.2, 131.2, 130.4, 129.0, 128.2, 128.2, 127.1, 127.0, 126.8, 125.7, 125.0, 113.2, 108.2, 105.7, 103.7, 52.5, 51.7, 50.2; HRMS (ESI) calcd for [$C_{27}H_{23}N_3O_2H^+$] 422.1863, found 422.1859.

Example 3

Methyl1-(4-methoxybenzyl)-4-(1-(4-methoxybenzyl)-1H-pyrrol-2-yl)-1H-pyrrolo[3,2-c]pyridine-6-carboxylate (3ba). According to the general procedure mentioned above, 1b (100 mg, 0.46 mmol), 2a (29 mg, 0.23 mmol) and DIPEA (0.140 mL, 0.81 mmol) were heated in a sealed tube at 150° C. for 6 h. After workup, the crude residue was purified through alumina (neutral, 175 mesh) column chromatography using hexane-EtOAc (88:12) as eluent; Yield 61% (68 mg); Yellow liquid; Rf 0.60 (1:1 hexane-EtOAc); IR (KBr) 3073 (=C—H), 2958-2851 (C—H), 1743 (C=O), 1109-1029 (C—O) cm-1; $^1$H NMR (400 MHz, CDCl$_3$) δ 8.04 (s, 1H), 7.22 (d, J=3.2 Hz, 1H), 7.08 (d, J=8.5 Hz, 2H), 7.02 (d, J=8.5 Hz, 2H), 6.90-6.81 (m, 4H), 6.78 (dd, J=3.5, 1.5 Hz, 1H), 6.69 (d, J=8.8 Hz, 2H), 6.25 (dd, J=3.3, 2.6 Hz, 1H), 5.77 (s, 2H), 5.28 (s, 2H), 3.97 (s, 3H), 3.78 (s, 3H), 3.69 (s, 3H); $^{13}$C NMR (100 MHz, CDCl$_3$) δ 166.7, 158.8, 157.8, 145.1, 139.6, 137.9, 130.9, 130.3, 129.6, 127.9, 127.8, 127.4, 124.7, 124.4, 113.7, 112.9, 112.5, 107.3, 105.0, 102.8, 54.6, 54.4, 51.7, 50.4, 49.0; HRMS (ESI) calcd for [$C_{29}H_{27}N_4O_3$+H$^+$] 482.2074, found 482.2074.

Example 4

Methyl1-methyl-4-(1-methyl-1H-pyrrol-2-yl)-1H-pyrrolo[3,2-c]pyridine-6-carboxylate (3ca). According to the general procedure mentioned above, 1c (100 mg, 0.92 mmol), 2a (29 mg, 0.46 mmol) and DIPEA (0.281 mL, 1.61 mmol) were heated in a sealed tube at 150° C. for 6 h. After workup, the crude residue was purified through alumina (neutral, 175 mesh) column chromatography using hexane-EtOAc (92:8) as eluent; Yield 48% (59 mg);Yellowish-brown liquid; Rf 0.60 (1:1 hexane-EtOAc); IR (KBr) 3126-3084 (=C—H), 2926-2852 (C—H), 1732 (C=O), 1714-1556 (C=C), 1350 (C—H bend), 721 (=CH bend) cm-1; $^1$H NMR (400 MHz, CDCl3) δ 8.04 (s, 1H), 7.24-7.17 (m, 1H), 6.89-6.81 (m, 1H), 6.80-6.74 (m, 1H), 6.73-6.68 (m, 1H), 6.25-6.13 (m, 1H), 4.03 (s, 3H), 3.97 (s, 3H), 3.85 (s, 3H); 13C NMR (100 MHz, CDCl$_3$) δ 167.5, 145.7, 140.7, 138.5, 132.0, 130.7, 126.2, 124.9, 112.6, 107.5, 105.5, 103.1, 52.5, 36.4, 33.1; HRMS (ESI) calcd for [$C_{15}H_{15}N_3O_2$+H$^+$] 270.1237, found 270.1233.

Example 5

Tert-butyl-1-benzyl-4-(1-benzyl-1H-pyrrol-2-yl)-1H-pyrrolo[3,2-c]pyridine-6-carboxylate (3ac). According to the general procedure mentioned above, 1a (100 mg, 0.54 mmol), 2c (45 mg, 0.27 mmol) and DIPEA (0.165 mL, 1.61 mmol) were heated in a sealed tube at 150° C. for 8 h. After workup, the crude residue was purified through alumina (neutral, 175 mesh) column chromatography using hexane-EtOAc (95:5) as eluent; Yield 40% (50 mg); Yellow liquid; Rf 0.50 (4:1 hexane-EtOAc); IR (KBr) 3063 (=C—H), 2976-2849 (C—H), 1732 (C=O), 1701-1564 (C=C), 1363 (C—H bend), 723 (=C—H bend) cm-1; $^1$H NMR (400 MHz, CDCl$_3$) δ 7.93 (s, 1H), 7.37-7.26 (m, 3H), 7.22 (d, J=3.2 Hz, 1H), 7.19-7.04 (m, 7H), 6.91 (d, J=3.2 Hz, 1H), 6.89-6.82 (m, 2H), 6.26 (dd, J=3.2, 3.0 Hz, 1H), 6.03 (s, 2H), 5.33 (s, 2H), 1.59 (s, 9H); $^{13}$C NMR (100 MHz, CDCl3) δ 166.0, 145.4, 140.7, 140.2, 139.8, 136.3, 130.9, 130.5, 129.0, 128.3, 128.1, 127.2, 127.0, 126.8, 125.8, 124.3, 113.3, 108.1, 105.0, 103.5, 81.1, 51.8, 50.1, 28.3; HRMS (ESI) calcd for [$C_{30}H_{29}N_3O_2$+H$^+$] 464.2333, found 464.2334.

Example 6

Ethyl1-methyl-4-(1-methyl-1H-pyrrol-2-yl)-1H-pyrrolo[3,2-c]pyridine-6-carboxylate (3cb). According to the general procedure mentioned above, 1c (100 mg, 0.92 mmol), 2b (64 mg, 0.46 mmol) and DIPEA (0.281 mL, 1.61 mmol) were heated in a sealed tube at 150° C. for 7 h. After workup, the crude residue was purified through alumina (neutral, 175 mesh) column chromatography using hexane-EtOAc (92:8) as eluent Yield 46% (60 mg); Light yellow liquid; Rf 0.50 (2:1 hexane-EtOAc); IR (KBr) 3077 (=C—H), 2957-2850 (C—H), 1731 (C=O), 1714-1558 (C=C), 1374 (C—H bend),725 (=C—H bend) cm-1; $^1$H NMR (400 MHz, CDCl$_3$) δ 8.04 (s, 1H), 7.24-7.19 (m, 1H), 6.92-6.85 (m, 1H), 6.83-6.78 (m, 1H), 6.78-6.72 (m, 1H), 6.27-6.19 (m, 1H), 4.46 (q, J=6.8 Hz, 2H), 4.10 (s, 3H), 3.88 (s, 3H), 1.45 (t, J=6.8 Hz, 3H); $^{13}$C NMR (100 MHz, CDCl$_3$) δ 166.9, 145.5, 140.7, 138.7, 131.9, 130.7, 126.3, 124.6, 112.7, 107.5, 105.2, 103.0, 61.3, 36.6, 33.1, 14.4; HRMS (ESI) calcd for [$C_{16}H_{17}N_3O_2$+H$^+$] 284.1394, found 284.1389.

Example 7

Ethyl1-benzyl-4-(1-benzyl-1H-pyrrol-2-yl)-1H-pyrrolo[3,2-c]pyridine-6-carboxylate (3ab). According to the general procedure mentioned above, 1a (100 mg, 0.54 mmol), 2b (38 mg, 0.27 mmol) and DIPEA (0.165 mL, 0.95 mmol) were heated in a sealed tube at 150° C. for 6 h. After workup, the crude residue was purified through alumina (neutral, 175 mesh) column chromatography using hexane-EtOAc (94:6) as eluent; Yield 55% (65 mg); Yellow liquid; Rf 0.60 (4:1 hexane-EtOAc); IR (KBr) 3056 (=C—H), 2977-2851 (C—H), 1729 (C=O), 1712-1554 (C=C), 1367 (C—H bend), 726 (=C—H bend) cm-1; $^1$H NMR (400 MHz, CDCl$_3$) δ 7.99 (s, 1H), 7.38-7.26 (m, 3H), 7.26-7.21 (m, 1H), 7.19-7.13 (m, 2H), 7.13-7.02 (m, 5H), 6.95-6.90 (m, 1H), 6.90-6.86 (m, 1H), 6.85-6.80 (m, 1H), 6.33-6.24 (m, 1H), 5.94 (s, 2H), 5.35 (s, 2H), 4.41 (q, J=6.8 Hz, 2H), 1.38 (t, J=6.8 Hz, 3H); $^{13}$C NMR (100 MHz, CDCl$_3$) δ 166.9, 145.7, 140.6, 139.7, 139.0, 136.3, 131.1, 130.4, 129.0, 128.3, 128.2, 127.2, 127.0, 126.8, 125.8, 124.8, 113.3, 108.2, 105.5, 103.6, 61.3, 51.7, 50.2, 14.4; HRMS (ESI) calcd for [$C_{28}H_{25}N_3O_2$+H+] 436.2020, found 436.2024.

Example 8

Ethyl 1-(4-methoxybenzyl)-4-(1-(4-methoxybenzyl)-1H-pyrrol-2-yl)-1H-pyrrolo[3,2-c]pyridine-6-carboxylate (3bb). According to the general procedure mentioned above, 1b (100 mg, 0.46 mmol), 2b (32 mg, 0.23 mmol) and DIPEA (0.140 mL, 0.81 mmol); Yield 60% (68 mg) were heated in a sealed tube at 150° C. for 8 h. After workup, the crude residue was purified through alumina (neutral, 175 mesh) column chromatography using hexane-EtOAc (90:10) as eluent; Yellow liquid; Rf 0.55 (2:1 hexane-EtOAc); IR (KBr) 3067 (=C—H), 2955-2852 (C—H), 1738 (C=O), 1713-1515 (C=C),1369 (C—H bend), 1106-1028 (C—O), 727 (=C—H bend) cm-1; 1H NMR (400 MHz, CDCl3) δ 8.03 (s, 1H), 7.21 (d, J=3 Hz, 1H), 7.08 (d, J=8.5 Hz, 2H), 7.05 (d, J=8.8 Hz, 2H), 6.88 (d, J=3.0 Hz, 1H), 6.87-6.82 (m, 3H), 6.80 (dd, J=3.3, 1.2 Hz, 1H), 6.69 (d, J=8.8 Hz, 2H), 6.26 (dd, J=3.0, 2.5 Hz, 1H), 5.83 (s, 2H), 5.28 (s, 2H), 4.43 (q, J=7.0 Hz, 2H), 3.78 (s, 3H), 3.70 (s, 3H), 1.40 (t, J=7.0 Hz, 3H); $^{13}$C NMR (100 MHz, CDCl$_3$) δ 167.0, 159.5, 158.5, 145.7, 140.4, 138.9, 131.7, 130.9, 130.3, 128.6, 128.6, 128.2, 125.4, 124.8, 114.4, 113.7, 113.2, 108.0, 105.5, 103.5, 61.3, 55.3, 55.2, 51.1, 49.7, 14.4; HRMS (ESI) calcd for [$C_{30}H_{29}N_3O_4$+H$^+$] 496.2231, found 496.2230.

Example 9

Tert-butyl 1-(4-methoxybenzyl)-4-(1-(4-methoxybenzyl)-1H-pyrrol-2-yl)-1H-pyrrolo[3,2-c]pyridine-6-carboxylate (3bc). According to the general procedure mentioned above, 1b (100 mg, 0.46 mmol), 2c (39 mg, 0.23 mmol) and DIPEA (0.140 mL, 0.81 mmol) were heated in a sealed tube at 150° C. for 7 h. After workup, the crude residue was purified through alumina (neutral, 175 mesh) column chromatography using hexane-EtOAc (9:1) as eluent; Yield 42% (50 mg); Yellow-orange oily liquid; Rf 0.55 (2:1 hexane-EtOAc); IR (KBr) 3066 (=C—H), 2995-2833 (C—H), 1730 (C=O), 1715-1554 (C=C), 1366 (C—H bend), 1113-1033 (C—O), 727 (=C—H bend) cm-1; $^1$H NMR (400 MHz, CDCl$_3$) δ 7.96 (s, 1H), 7.19 (d, J=3.3 Hz, 1H), 7.08 (d, J=8.6 Hz, 2H), 7.04 (d, J=8.5 Hz, 2H), 6.88 (d, J=3.3 Hz, 1H), 6.87-6.79 (m, 4H), 6.69 (d, J=8.5 Hz, 2H), 6.25 (dd, J=3.5, 2.4 Hz, 1H), 5.93 (s, 2H), 5.26 (s, 2H), 3.78 (s, 3H), 3.69 (s, 3H), 1.61 (s, 9H); $^{13}$C NMR (100 MHz, CDCl3) δ 166.1, 159.5, 158.5, 145.4, 140.6, 140.1, 131.8, 130.7, 130.4, 128.7, 128.6, 128.3, 125.5, 124.3, 114.4, 113.7, 113.3, 108.0, 105.0, 103.4, 81.1, 55.3, 55.2, 51.3, 49.7, 28.3; HRMS (ESI) calcd for [C$_{32}$H$_{33}$N$_3$O$_4$+H$^+$] 524.2544, found 524.2551.

Example 10

Methyl 1-tosyl-4-(1-tosyl-1H-pyrrol-2-yl)-1H-pyrrolo[3,2-c]pyridine-6-carboxylate (3da). According to the general procedure mentioned above, 1d (100 mg, 0.40 mmol), 2a (25 mg, 0.20 mmol) and DIPEA (0.122 mL, 0.70 mmol) were heated in a sealed tube at 150° C. for 12 h. After workup, the crude residue was purified through alumina (neutral, 175 mesh) column chromatography using hexane-EtOAc (85:15) as eluent; Yield 47% (52 mg); Off white solid; m.p.=120-122° C.; Rf 0.50 (1:1 hexane-EtOAc); IR (KBr) 3132-3064 (=C—H), 2955-2850 (C—H), 1728 (C=O), 1710-1512 (C=C), 1371 (C—H bend), 1309 (N—S=O), 1145 (S=O), 725 (=C—H bend) cm-1; $^1$H NMR (400 MHz, CDCl3) δ 8.72 (s, 1H), 7.93 (d, J=8.0 Hz, 2H), 7.86 (d, J=8.3 Hz, 2H), 7.70 (d, J=3.8 Hz, 1H), 7.41-7.36 (m, 1H), 7.32 (d, J=8.0 Hz, 2H), 7.29-7.25 (m, 2H), 6.66 (d, J=3.8 Hz, 1H), 6.41-6.36 (m, 1H), 6.33 (dd, J=3.3, 2.6 Hz, 1H), 4.03 (s, 3H), 2.40 (s, 3H), 2.38 (s, 3H); $^{13}$C NMR (100 MHz, CDCl$_3$) δ 166.1, 146.2, 145.5, 145.0, 142.0, 139.3, 136.0, 134.8, 131.0, 130.5, 130.2, 129.8, 129.3, 128.3, 127.2, 124.3, 117.3, 112.2, 110.2, 108.1, 53.0, 29.8, 21.7; HRMS (ESI) calcd for [C$_{27}$H$_{23}$N$_3$O$_6$S$_2$+H$^+$] 550.1101, found 550.1096.

Example 11

Methyl 1-(phenylsulfonyl)-4-(1-(phenylsulfonyl)-1H-pyrrol-2-yl)-1H-pyrrolo[3,2-c]pyridine-6-carboxylate (3ea). According to the general procedure mentioned above, 1e (100 mg, 0.43 mmol), 2a (27 mg, 0.21 mmol) and DIPEA (0.128 mL, 0.74 mmol) were heated in a sealed tube at 150° C. for 12 h. After workup, the crude residue was purified through alumina (neutral, 175 mesh) column chromatography using hexane-EtOAc (85:15) as eluent; Yield 45% (49 mg); Yellow solid; m.p.=104-106° C.; Rf 0.50 (1:1 hexane-EtOAc); IR (KBr) 3132-3064 (=C—H), 3005-2850 (C—H), 1728 (C=O), 1710-1512 (C=C), 1371 (C—H bend), 1309 (N—S=O), 1145 (S=O), 725 (=C—H bend) cm-1; $^1$H NMR (400 MHz, CDCl$_3$) δ 8.74 (s, 1H), 8.06 (d, J=7.5 Hz, 2H), 7.99 (d, J=7.5 Hz, 2H), 7.71 (d, J=3.8 Hz, 1H), 7.67-7.43 (m, 6H), 7.40 (dd, J=3.0, 1.5 Hz, 1H), 6.67 (d, J=3.8 Hz, 1H), 6.42 (dd, J=3.0, 1.5 Hz, 1H), 6.35 (dd, J=3.3, 2.5 Hz, 1H), 4.01 (s, 3H); $^{13}$C NMR (100 MHz, CDCl$_3$) δ 166.0, 145.3, 142.1, 139.3, 139.0, 137.7, 134.8, 133.8, 131.0, 129.8, 129.6, 129.3, 129.1, 128.1, 127.1, 124.4, 117.5, 112.3, 110.1, 108.2, 52.9; HRMS (ESI) calcd for [C$_{25}$H$_{19}$N$_3$O$_6$S$_2$+Na+] 544.0607, found 544.0603.

Example 12

Methyl 1-benzyl-4-(1-benzyl-5-methyl-1H-pyrrol-2-yl)-2-methyl-1H-pyrrolo[3,2-c]pyridine-6-carboxylate (3fa). According to the general procedure mentioned above, 1f (100 mg, 0.50 mmol), 2a (32 mg, 0.25 mmol) and DIPEA (0.150 mL, 0.88 mmol) were heated in a sealed tube at 150° C. for 6 h. After workup, the crude residue was purified through alumina (neutral, 175 mesh) column chromatography using hexane-EtOAc (90:10) as eluent; Yield 64% (72 mg); Yellow liquid; Rf 0.55 (2:1 hexane-EtOAc); IR (KBr) 3027 (=C—H), 2949-2852 (C—H), 1727 (C=O), 1712-1539 (C=C), 1355 (C—H bend), 782 (=C—H bend) cm-1; $^1$H NMR (400 MHz, CDCl3) δ 7.88 (s, 1H), 7.43-7.26 (m, 3H), 7.19-7.01 (m, 3H), 6.99-6.90 (m, 2H), 6.89-6.82 (m, 2H), 6.80-6.66 (m, 2H), 6.12-6.02 (m, 1H), 5.92 (s, 2H), 5.33 (s, 2H), 3.87 (s, 3H), 2.38 (s, 3H), 2.22 (s, 3H); $^{13}$C NMR (100 MHz, CDCl3) δ$^{13}$C NMR (100 MHz, CDCl3) δ 167.5, 144.7, 141.4, 140.5, 139.9, 138.0, 136.5, 133.2, 130.4, 129.5, 129.0, 128.2, 127.7, 126.3, 126.1, 126.0, 112.3, 107.5, 105.1, 102.5, 52.3, 47.8, 46.8, 12.9, 12.7; HRMS (ESI) calcd for [C$_{29}$H$_{27}$N$_3$O$_2$+H$^+$] 450.2176, found 450.2173.

Example 13

1-Benzyl-4-(1-benzyl-1H-pyrrol-2-yl)-1H-pyrrolo[3,2-c]pyridine-6-carboxamide (11). In a round-bottom flask (100 mL), Methyl 1-benzyl-4-(1-benzyl-1H-pyrrol-2-yl)-1H-pyrrolo[3,2-c]pyridine-6-carboxylate (3aa,100 mg,0.24 mmol) and KOH (14 mg, 0.24 mmol) was dissolved in methanol (5 mL) at room temperature under continuous stirring. Aqueous ammonia (25%, 0.350 mL, 9.40 mmol) was added to the mixture dropwise using a glass syringe over a period of 10 min. The reaction mixture was stirred at the room temperature for further 24 h. After the completion of the reaction, MeOH was evaporated under reduced pressure. MilliQ water (5 mL) and EtOAc (5 mL) was added to the residue and organic layer was separated. The aqueous phase was further extracted with EtOAc (5×3 mL). The combined organic layers were dried over anhydrous Na$_2$SO$_4$, filtered, and concentrated under reduced pressure. The residue was purified using EtOAc as eluent over neutral alumina (175 mesh) column chromatography; Yield 78% (150 mg); Yellow gummy liquid; Rf 0.50 (EtOAc); IR (KBr) 3431 (N—H), 3033 (=C—H), 2960-2852 (C—H), 1677 (C=O), 1562 (C—N bend), 1376-1360 (C—H bend), 1296-1029 (C—O), 726 (=C—H bend) cm-1; $^1$H NMR (400 MHz, CDCl3) δ 8.07 (s, 1H), 7.38-7.19 (m, 7H), 7.16-7.06 (m, 3H), 6.95 (d, J=3.0 Hz, 1H), 6.92-6.85 (m, 2H), 6.85-6.78 (m, 1H), 6.40 (dd, J=3.0, 2.6 Hz, 1H), 5.59 (s, 2H), 5.38 (s, 2H), 4.89 (brs, 2H); $^{13}$C NMR (100 MHz, CDCl3) δ 168.1, 144.1, 141.1, 140.0, 136.3, 131.0, 129.0, 129.0, 128.7, 128.1, 127.0, 127.0, 126.9, 126.1, 125.3, 124.9, 112.6, 108.8, 103.5, 103.0, 51.3, 50.2; MS (ESI) calcd for [C$_{26}$H$_{22}$N$_4$O+H$^+$] 407.1866, found 407.2023.*

*The compound 11 is unstable in polar solvent to record a good HRMS.

Example 14

1-Benzyl-4-(1-benzyl-1H-pyrrol-2-yl)-1H-pyrrolo[3,2-c]pyridine-6-carbonitrile (12). An oven-dried single neck round-bottom flask (25 mL) was charged with 1-Benzyl-4-

(1-benzyl-1H-pyrrol-2-yl)-1H-pyrrolo[3,2-c]pyridine-6-carboxamide (11, 40 mg, 0.098 mmol) and POCl$_3$ (5 mL) was added dropwise using a glass syringe over a period of 20 min at room temperature. A reflux condenser was fixed to the round bottom flask and the reaction mixture was heated at 60° C. and stirred for overnight. After the completion of the reaction (monitored by TLC), the reaction mixture was diluted with toluene (5 mL) and the solvent was evaporated under reduced pressure. Saturated NaHCO$_3$ (10 mL) was added slowly to the reaction mixture to neutralize excess phosphorous oxychloride. The aqueous phase was extracted with EtOAc (5×3 mL). The combined organic layers were dried over anhydrous Na$_2$SO$_4$, filtered, and concentrated under reduced pressure. The residue was purified using hexane-EtOAC (90:10) as eluent over neutral alumina (175 mesh) column chromatography to afford 12; Yield 66% (25 mg); colorless liquid; Rf 0.20 (2:1 hexane-EtOAc); IR (KBr) 3431 (N—H), 3031 (=C—H), 2960-2852 (C—H), 2223 (=C—N stretch), 1588-1530 (C=C), 1376-1360 (C—H bend), 725 (=C—H bend) cm-1; $^1$H NMR (400 MHz, CDCl$_3$) δ 7.43 (s, 1H), 7.39-7.31 (m, 3H), 7.30 (d, J=3.0 Hz, 1H), 7.22-7.02 (m, 7H), 6.94 (d, J=3.0 Hz, 1H), 6.93-6.89 (m, 1H), 6.85 (dd, J=3.5, 1.2 Hz, 1H), 6.31 (dd, J=3.0, 2.4 Hz, 1H), 5.75 (s, 2H), 5.31 (s, 2H); $^{13}$C NMR (100 MHz, CDCl3) δ 147.3, 139.2, 135.5, 131.7, 129.5, 129.2, 128.5, 128.5, 128.4, 127.2, 127.0, 126.9, 126.6, 124.6, 123.1, 119.2, 114.1, 109.1, 108.4, 104.1, 52.1, 50.6; HRMS (ESI) calcd for [C$_{26}$H$_{20}$N$_4$+H$^+$] 389.1761, found 389.1777.

Example 15

1-Benzyl-4-(1-benzyl-1H-pyrrol-2-yl)-1H-pyrrolo[3,2-c]pyridin-6-yl)methanol (13). In a two-neck round-bottom flask (50 mL), Methyl 1-benzyl-4-(1-benzyl-1H-pyrrol-2-yl)-1H-pyrrolo[3,2-c]pyridine-6-carboxylate (3aa, 250 mg, 0.59 mmol) was dissolved in dry THF (5 mL) under an inert atmosphere. The reaction mixture was cooled to 0° C. before addition of solid LiAlH4 (68 mg, 1.78 mmol) in single portion. The reaction mixture was warmed to room temperature and further stirred for 20 min. After the consumption of ester 3aa, as confirmed by TLC, the reaction mixture was quenched with saturated NH$_4$Cl (10 mL) solution and further diluted with EtOAc (10 mL). The aqueous layer was extracted using EtOAc (10×3 mL). The combined organic extracts were dried over anhydrous Na$_2$SO$_4$, filtered, evaporated under reduced pressure, and the crude residue was purified over neutral alumina (175 mesh) column chromatography using hexane-EtOAC (75:25) as eluent; Yield 94% (220 mg); colorless liquid; Rf 0.35 (2:1 hexane-EtOAc); IR (KBr) 3414 (O—H), 3028 (=C—H), 2958-2850 (C—H), 1695-1559 (C=C), 1357 (C—H bend), 1100-1023 (C—O stretch) cm-1; $^1$H NMR (400 MHz, CDCl3) δ 7.36-7.17 (m, 6H), 7.13 (d, J=3.3 Hz, 1H), 7.07 (dd, J=7.5, 8.0 Hz, 4H), 6.90 (s, 1H), 6.89-6.80 (m, 3H), 6.36 (dd, J=3.0, 2.6 Hz, 1H), 5.65 (s, 2H), 5.28 (s, 2H), 4.63 (s, 2H), 3.24 (brs, 1H);$^{13}$C NMR (100 MHz, CDCl3) δ 149.6, 144.7, 141.6, 139.7, 136.6, 131.1, 129.2, 129.0, 128.5, 128.0, 127.0, 126.8, 126.3, 125.2, 122.7, 112.6, 108.5, 103.0, 99.0, 64.7, 51.7, 50.1; HRMS (ESI) calcd for [C$_{26}$H$_{23}$N$_3$O+H$^+$] 394.1914, found 394.1913.

Example 16

1-Benzyl-4-(1-benzyl-1H-pyrrol-2-yl)-1H-pyrrolo[3,2-c]pyridine-6-carbaldehyde (14). A solution of (1-benzyl-4-(1-benzyl-1H-pyrrol-2-yl)-1H-pyrrolo[3,2-c]pyridin-6-yl)methanol (13, 100 mg, 0.25 mmol) was prepared in dichloromethane (5 mL) in around-bottom flask (100 mL) and solid MnO$_2$ (326 mg, 3.75 mmol) was added in single portion. A double-walled reflux condenser was fixed to the round-bottom flask and reaction mixture was refluxed overnight. After the completion of reaction, solvent was evaporated under reduced pressure. The residual mixture was purified over neutral alumina (175 mesh) column chromatography using hexane-EtOAc (95:5) as eluent; Yield 70% (70 mg); Off white liquid; Rf 0.55 (2:1 hexane-EtOAc); IR (KBr) 3030 (=C—H), 2960-2852 (C—H), 1696 (C=O), 1606-1556 (C=C), 1358-1331 (=C—H bend), 1287-1079 (C—O), 725 (=C—H bend) cm-1; $^1$H NMR (400 MHz, CDCl3) δ 10.02 (s, 1H), 7.83 (s, 1H), 7.42-7.27 (m, 4H),* 7.23-7.02 (m, 7H), 6.98-6.93 (m, 1H), 6.92-6.88 (m, 1H), 6.88-6.82 (m, 1H), 6.42-6.28 (m, 1H), 5.81 (s, 2H), 5.36 (s, 2H); $^{13}$C NMR (100 MHz, CDCl3) δ 194.3, 146.3, 145.1, 140.4, 139.5, 136.0, 132.3, 130.3, 129.1, 128.4, 128.3, 127.0*, 126.8, 126.2, 125.9, 113.3, 108.5, 103.7, 102.2, 51.9, 50.4; HRMS (ESI) calcd for [C$_{26}$H$_{21}$N$_3$O+H$^+$] 392.1757, found 392.1756.*higher intensity carbon Example 17

1-Methyl-4-(1-methyl-1H-pyrrol-2-yl)-1H-pyrrolo[3,2-c]pyridine-6-carboxylic acid (15). Around-bottom flask (50 mL) was charged with Methyl 1-methyl-4-(1-methyl-1H-pyrrol-2-yl)-1H-pyrrolo[3,2-c]pyridine-6-carboxylate (3ca, 200 mg, 0.74 mmol) dissolved in THF (3 mL). 1M aqueous LiOH solution (2.5 mL) was added at room temperature and the reaction mixture was stirred for 3 h at the same temperature (monitored by TLC). After the consumption of 3ca, diethyl ether (10 mL) and saturated NaHCO$_3$ (10 mL) was added to the reaction mixture. The aqueous layer was separated and acidified to pH 4 (by dropwise addition of 6N HCl). The aqueous phase was extracted with EtOAc (5×10 mL). The combined organic layers were dried over anhydrous Na2SO4, filtered, and evaporated under reduced pressure to give crude product 15 which was utilized in the next step without further purification; Crude yield 90% (172 mg); Yellow oily liquid; Rf 0.10 (EtOAc); $^1$H NMR (400 MHz, CDCl3) δ 8.14 (s, 1H), 7.32 (d, J=3.0 Hz, 1H), 6.90 (d, J=3.0 Hz, 1H), 6.86 (m, 1H), 6.77 (dd, J=3.5, 1.3 Hz, 1H), 6.29 (dd, J=2.8, 2.4 Hz, 1H), 3.94 (s, 3H), 3.91 (s, 3H); $^{13}$C NMR (100 MHz, CDCl3) δ 164.8, 142.8, 140.3, 135.8, 132.0, 128.2, 125.8, 124.5, 112.6, 107.3, 102.9, 102.7, 35.3, 32.3; HRMS (ESI) calcd for [C$_{14}$H$_{13}$N$_3$O$_2$+H$^+$] 256.1081, found 256.1066.

Example 18

1-Methyl-4-(1-methyl-1H-pyrrol-2-yl)-1H-pyrrolo[3,2-c]pyridin-6-yl)(morpholino)methanone (16). A two-neck round-bottom flask (50 mL) was charged with unpurified 15 (100 mg, 0.39 mmol) dissolved in dry DMF (4 mL) under an inert atmosphere. The reaction mixture was cooled briefly to 0° C. before addition of morpholine (0.13 mL, 1.57 mmol), 1-ethyl-3-(3-dimethylaminopropyl)carbodiimide (300 mg, 1.57 mmol), hydroxybenzotriazole (212 mg, 1.57 mmol) and DIPEA (0.54 mL, 3.13 mmol) in a sequential manner under constant stirring. The reaction mixture was warmed to room temperature, stirred for further 16 h. After the consumption of 15 as confirmed by TLC, cold brine (10 mL) was added to the reaction mixture. The reaction mixture was extracted with EtOAc (10×3 mL) and the combined organic layers were dried over anhydrous Na2SO4, filtered, concentrated, and purified over neutral alumina (175 mesh) column chromatography using hexane-EtOAc (50:50) as eluent;

Yield 49% (60 mg); White crystalline solid; m.p.=95-96° C.; Rf 0.40 (1:1 hexane-EtOAc); IR (KBr) 3065 (=C—H), 2957-2850 (C—H),1682 (C=O), 1641-1513 (C=C),1371 (C—H bend), 723 (=C—H bend) cm-1; $^1$H NMR (400 MHz, CDCl$_3$) δ 7.65 (s, 1H), 7.17 (d, J=3.0 Hz, 1H), 6.82 (d, J=3.0 Hz, 1H), 6.80-6.77 (m, 1H), 6.76-6.71 (m, 1H), 6.25 (dd, J=2.8, 2.4 Hz, 1H), 3.97 (s, 3H), 3.92-3.76 (m, 9H), 3.72-3.60 (m, 2H); $_{13}$C NMR (100 MHz, CDCl3) δ 169.2, 144.2, 144.1, 141.1, 131.1, 130.9, 125.9, 123.4, 112.6, 107.6, 104.3, 102.8, 67.3, 67.0, 48.1, 43.1, 36.6, 32.9; HRMS (ESI) calcd for [C$_{18}$H$_{20}$N$_4$O$_2$+H+] 325.1659, found 325.1655.

Example 19

Methyl 5-methyl-1-(1-methyl-1H-indol-2-yl)-5H-pyrido[4,3-b]indole-3-carboxylate (18aa). According to the general procedure mentioned above, 17a (100 mg, 0.62 mmol), 2a (39 mg, 0.31 mmol) and DIPEA (0.190 mL, 1.09 mmol) were heated in a sealed tube at 120° C. for 6 h. After workup, crude was purified through alumina (neutral, 175 mesh) column chromatography using hexane-EtOAc (80:20) as eluent; Yield 70% (80 mg); Yellow solid; m.p.=210-212° C.; Rf 0.35 (2:1 hexane-EtOAc); IR (KBr) 3055 (=C—H), 2956-2854 (C—H), 1734 (C=O), 1687-1534 (C=C), 1407-1376 (C—H bend), 782 (=C—H bend) cm-1; $^1$H NMR (400 MHz, CDCl$_3$) δ 8.31 (s, 1H), 7.82 (d, J=8.0 Hz, 1H), 7.74 (d, J=8.0 Hz, 1H), 7.56 (dd, J=8.0, 7.3 Hz, 1H), 7.51 (d, J=8.3 Hz, 1H), 7.45 (d, J=8.3 Hz, 1H), 7.33 (dd, J=8.0, 7.8 Hz, 1H), 7.19 (dd, J=7.5, 7.5 Hz, 1H), 7.15 (dd, J=7.5, 7.6 Hz, 1H), 6.99 (s, 1H), 4.05 (s, 3H), 4.00 (s, 3H), 3.75 (s, 3H); $^{13}$C NMR (100 MHz, CDCl$_3$) δ 166.9, 146.3, 145.8, 142.9, 142.2, 138.3, 137.6, 128.1, 127.9, 123.1, 122.4, 121.3, 121.2, 121.1, 120.8, 119.8, 109.8, 109.1, 105.7, 104.3, 53.0, 31.0, 29.6; HRMS (ESI) calcd for [C$_{23}$H$_{19}$N$_3$O$_2$+H+] 370.1550, found 370.1515.

Example 20

Ethyl 5-methyl-1-(1-methyl-1H-indol-2-yl)-5H-pyrido[4,3-b]indole-3-carboxylate (18ab). According to the general procedure mentioned above, 17a (100 mg, 0.62 mmol), 2b (43 mg, 0.31 mmol) and DIPEA (0.190 mL, 1.09 mmol) were heated in a sealed tube at 120° C. for 6 h. After workup, crude was purified through alumina (neutral, 175 mesh) column chromatography using hexane-EtOAc (85:15) as eluent; Yield 66% (78 mg); Yellow solid; m.p.=175-177° C.; Rf 0.40 (2:1 hexane-EtOAc); IR (KBr) 3058 (=C—H), 2988-2851 (C—H), 1735 (C=O), 1704-1536 (C=C), 1409-1375 (C—H bend), 780 (=C—H bend) cm-1; $^1$H NMR (400 MHz, CDCl3) δ 8.27 (s, 1H), 7.89 (d, J=8.0 Hz, 1H), 7.73 (d, J=7.8 Hz, 1H), 7.56 (dd, J=7.8, 7.3 Hz, 1H), 7.50 (d, J=8.0 Hz, 1H), 7.46 (d, J=8.0 Hz, 1H), 7.33 (dd, J=7.8, 7.8 Hz, 1H), 7.19 (m, 2H), 7.01 (s, 1H), 4.53 (q, J=7.0 Hz, 2H), 3.99 (s, 3H), 3.79 (s, 3H), 1.48 (t, J=7.0 Hz, 3H); $^{13}$C NMR (100 MHz, CDCl$_3$) δ 166.3, 146.3, 145.9, 143.2, 142.2, 138.3, 137.6, 128.0, 127.8, 123.1, 122.4, 121.2, 121.1, 120.9, 120.8, 119.8, 109.8, 109.1, 105.5, 104.4, 61.9, 31.1, 29.5, 14.5; HRMS (ESI) calcd for [C$_{24}$H$_{21}$N$_3$O$_2$+H+] 384.1707, found 384.1672.

Example 21

Tert-butyl 5-methyl-1-(1-methyl-1H-indol-2-yl)-5H-pyrido[4,3-b]indole-3-carboxylate (18ac). According to the general procedure mentioned above, 17a (100 mg, 0.62 mmol), 2c (52 mg, 0.31 mmol) and DIPEA (0.190 mL, 1.09 mmol) were heated in a sealed tube at 120° C. for 8 h. After workup, crude reaction mixture was purified through alumina (neutral, 175 mesh) column chromatography using hexane-EtOAc (90:10) as eluent; Yield 67% (85 mg); yellow solid; m.p.=200-202° C.; Rf 0.60 (2:1 hexane-EtOAc); IR (KBr) 3053 (=C—H), 2972-2852 (C—H), 1729 (C=O), 1686-1532 (C=C), 1412-1365 (C—H bend), 781 (=C—H bend) cm-1; $^1$H NMR (400 MHz, CDCl$_3$) δ 8.14 (s, 1H), 8.08 (d, J=7.0 Hz, 1H), 7.73 (d, J=6.5 Hz, 1H), 7.61-7.41 (m, 3H), 7.37-7.28 (m, 1H), 7.23-7.11 (m, 2H), 7.06 (s, 1H), 3.97 (s, 3H), 3.89 (s, 3H), 1.69 (s, 9H); $^{13}$C NMR (100 MHz, CDCl3) δ 165.2, 146.2, 146.1, 144.3, 142.2, 138.4, 137.7, 127.8, 127.7, 123.1, 122.4, 121.2, 120.9*, 120.3, 119.7, 109.8, 109.0, 104.7, 104.6, 81.9, 31.2, 29.5, 28.3; HRMS (ESI) calcd for [C$_{26}$H$_{25}$ N$_3$O$_2$+H+]412.1947, found 412.2012. *higher intensity carbon

Example 22

Methyl 5-benzyl-1-(1-benzyl-1H-indol-2-yl)-5H-pyrido[4,3-b]indole-3-carboxylate (18ba). According to the general procedure mentioned above, 17b (0.100 g, 0.42 mmol), 2a (26 mg, 0.21 mmol) and DIPEA (0.095 mL, 0.74 mmol) were heated in a sealed tube at 120° C. for 6 h. After workup, crude was purified through alumina (neutral, 175 mesh) column chromatography using hexane-EtOAc (85:15) as eluent; Yield 58% (63 mg); Yellow solid; m.p.=168-170° C.; Rf 0.60 (2:1 hexane-EtOAc); IR (ATR) 3062 (=C—H), 2920-2850 (C—H), 1710 (C=O), 1667-1528 (C=C), 1467-1315 (C—H bend), 787-694 (=C—H bend) cm-1; $^1$H NMR (400 MHz, CDCl$_3$) δ 8.20 (s, 1H), 8.13 (d, J=8.0 Hz, 1H), 7.75 (d, J=7.5 Hz, 1H), 7.48 (dd, J=7.5, 7.3 Hz, 1H), 7.41 (m, 2H), 7.35-7.23 (m, 4H), 7.20 (d, J=7.5 Hz, 1H), 7.16 (d, J=8.0 Hz, 1H), 7.14-7.08 (m, 3H), 6.99-6.89 (m, 5H), 5.67 (s, 2H), 5.60 (s, 2H), 3.98 (s, 3H); $^{13}$C NMR (100 MHz, CDCl$_3$) δ 166.8, 146.5, 145.8, 142.9, 141.7, 138.3, 138.1, 136.9, 135.6, 129.0, 128.1*, 128.0, 127.9, 126.7, 126.6, 126.3, 123.3, 122.7, 121.3, 121.13, 121.06, 121.0, 120.0, 110.6, 109.6, 105.7, 105.5, 52.9, 47.7, 46.8; HRMS (ESI) calcd for [C$_{35}$H$_{27}$N$_3$O$_2$+H+] 522.2176, found 522.2160.*Higher intensity carbon

Example 23

Ethyl 5-benzyl-1-(1-benzyl-1H-indol-2-yl)-5H-pyrido[4,3-b]indole-3-carboxylate (18bb). According to the general procedure mentioned above, 17b (0.100 g, 0.62 mmol), 2b (43 mg, 0.31 mmol) and DIPEA (0.190 mL, 1.09 mmol) were heated in a sealed tube at 120° C. for 6 h. After workup, crude was purified through alumina (neutral, 175 mesh) column chromatography using hexane-EtOAc (80:20) as eluent; Yield 66% (78 mg); Reddish yellow liquid; Rf 0.40 (2:1 hexane-EtOAc); IR (KBr) 3059 (=C—H), 2965-2860 (C—H), 1722 (C=O), 1609-1574 (C=C), 1423-1383 (C—H bend), 799 (=C—H bend) cm-1; $^1$H NMR (400 MHz, CDCl$_3$) δ 8.21-8.14 (m, 2H), 7.75 (d, J=7.5 Hz, 1H),7.47 (dd, J=7.8, 7.3 Hz, 1H),7.40 (m, 2H), 7.35-7.23 (m, 4H), 7.20 (d, J=7.3 Hz, 1H), 7.16 (d, J=7.3 Hz, 1H),7.14-7.08 (m, 3H), 7.02-6.89 (m, 5H), 5.72 (s, 2H), 5.59 (s, 2H), 4.45 (q, J=7.1 Hz, 2H), 1.40 (t, J=7.1 Hz, 3H); $^{13}$C NMR (100 MHz, CDCl$_3$) δ 166.2, 146.5, 145.9, 143.2, 141.7, 138.4, 138.1, 136.9, 135.7, 129.0, 128.2, 128.1, 128.0, 127.8, 126.7, 126.6, 126.4, 123.3, 122.7, 121.2, 121.1, 121.0, 120.9, 120.0, 110.6, 109.6, 105.52, 105.48, 61.8, 47.7, 46.8, 14.4; HRMS (ESI) calcd for [C$_{36}$H$_{29}$N$_3$O$_2$+H$^±$] 536.2333, found 536.2349.

Example 24

Tert-butyl 5-benzyl-1-(1-benzyl-1H-indol-2-yl)-5H-pyrido[4,3-b]indole-3-carboxylate (18bc). According to the general procedure mentioned above, 17b (0.100 g, 0.62 mmol), 2c (52 mg, 0.31 mmol) and DIPEA (0.190 mL, 1.09 mmol) were heated in a sealed tube at 120° C. for 8 h. After workup, crude was purified through alumina (neutral, 175 mesh) column chromatography using hexane-EtOAc (85: 15) as eluent; Yield 66% (84 mg); Yellow solid; m.p.=148-150° C.; Rf 0.60 (2:1 hexane-EtOAc); IR (ATR) 3062 (=C—H), 2926-2848 (C—H), 1706 (C=O), 1665-1531 (C=C), 1495-1323 (C—H bend), 782-694 (=C—H bend) cm-1; $^1$H NMR (400 MHz, CDCl$_3$) δ 8.28 (d, J=8.0 Hz, 1H), 8.06 (s, 1H), 7.75 (d, J=7.8 Hz, 1H), 7.47 (dd, J=7.5, 7.3 Hz, 1H), 7.43-7.36 (m, 2H), 7.34-7.22 (m, 4H), 7.21-7.15 (m, 2H), 7.15-7.10 (m, 3H), 7.02-6.93 (m, 5H), 5.86 (s, 2H), 5.58 (s, 2H), 1.63 (s, 9H); $^{13}$C NMR (100 MHz, CDCl$_3$) δ 165.2, 146.4, 146.1, 144.5, 141.7, 138.6, 138.1, 137.0, 135.8, 129.0, 128.2, 128.0, 127.84, 127.75, 126.7, 126.5, 126.4, 123.3, 122.7, 121.2, 121.1, 120.9, 120.4, 120.0, 110.6, 109.6, 105.7, 104.9, 81.8, 47.5, 46.8, 28.2; HRMS (ESI) calcd for [C$_{38}$H$_{33}$N$_3$O$_2$+H$^+$] 564.2646, found 564.2644.

Example 25

Methyl 8-methoxy-1-(5-methoxy-1-methyl-1H-indol-2-yl)-5-methyl-5H-pyrido[4,3-b]indole-3-carboxylate (18ca). According to the general procedure mentioned above, 17c (70 mg, 0.37 mmol), 2a (23 mg, 0.18 mmol) and DIPEA (0.110 mL, 0.63 mmol) were heated in a sealed tube at 120° C. for 3 h. After workup, crude was purified through alumina (neutral, 175 mesh) column chromatography using hexane-EtOAc (85:15) as eluent; Yield 66% (84 mg); Yellow solid; m.p.=160-162° C.; Rf 0.60 (2:1 hexane-EtOAc); IR (ATR) 3070 (=C—H), 2957-2850 (C—H), 1701 (C=O), 1660-1528 (C=C), 1485-1329 (C—H bend), 1105-991 (C—O), 810-688 (=C—H bend) cm-1; $^1$H NMR (400 MHz, CDCl$_3$) δ 8.26 (s, 1H), 7.40 (d, J=9.8 Hz, 1H), 7.32 (d, J=8.8 Hz, 1H), 7.21-7.16 (m, 2H), 7.15 (d, J=2.0 Hz, 1H), 6.97 (dd, J=9.0 Hz, 2.3 Hz, 1H), 6.91 (s, 1H), 4.05 (s, 3H), 3.96 (s, 3H), 3.89 (s, 3H), 3.71 (s, 3H), 3.55 (s, 3H); $^{13}$C NMR (100 MHz, CDCl$_3$) δ 167.0, 154.8, 154.3, 146.3, 145.8, 142.6, 137.9, 137.2, 133.8, 128.1, 121.2, 120.8, 117.7, 112.8, 110.4, 109.9, 105.8, 105.0, 103.8, 102.5, 55.8, 55.7, 53.0, 31.1, 29.6; HRMS (ESI) calcd for [C$_{25}$H$_{23}$N$_3$O$_4$+H$^+$] 430.1761, found 430.1764.

Example 26

Methyl 5-(4-methoxybenzyl)-1-(1-(4-methoxybenzyl)-1H-indol-2-yl)-5H-pyrido[4,3-b]indole-3-carboxylate (18da). According to the general procedure mentioned above, 17d (0.100 g, 0.38 mmol), 2a (24 mg, 0.19 mmol) and DIPEA (0.120 mL, 0.66 mmol) were heated in a sealed tube at 120° C. for 3 h. After workup, crude was purified through alumina (neutral, 175 mesh) column chromatography using hexane-EtOAc (85:15) as eluent; Yield 66% (84 mg); Yellow solid; m.p.=106-108° C.; Rf 0.60 (2:1 hexane-EtOAc); IR (ATR) 3056 (=C—H), 2952-2835 (C—H), 1737 (C=O), 1664-1512 (C=C), 1457-1348 (C—H bend), 1106-989 (C—O), 819-695 (=C—H bend) cm-1; $^1$H NMR (400 MHz, CDCl$_3$) δ 8.22 (s, 1H), 8.04 (d, J=8.0 Hz, 1H), 7.73 (d, J=7.8 Hz, 1H), 7.51-7.39 (m, 3H), 7.27 (d, J=7.3 Hz, 1H), 7.18 (dd, J=7.5, 7.0 Hz, 1H), 7.12 (dd, J=7.3, 7.3 Hz, 1H), 7.07 (d, J=8.5 Hz, 1H), 7.06 (s, 1H), 6.85 (d, J=8.8 Hz, 2H), 6.83 (d, J=8.8 Hz, 2H), 6.45 (d, J=8.5 Hz, 2H), 5.55 (s, 2H), 5.54 (s, 2H), 3.99 (s, 3H), 3.76 (s, 3H), 3.52 (s, 3H); $^{13}$C NMR (100 MHz, CDCl$_3$) δ 166.9, 159.4, 158.4, 146.6, 145.7, 142.9, 141.7, 138.0, 137.0, 130.4, 128.1, 127.95, 127.92, 127.75, 127.68, 123.3, 122.6, 121.2, 121.1, 121.04, 121.01, 119.9, 114.5, 113.5, 110.6, 109.6, 105.7, 105.3, 55.3, 55.1, 52.9, 47.2, 46.4; HRMS (ESI) calcd for [C$_{37}$H$_{31}$N$_3$O$_4$+H$^+$] 582.2387, found 582.2373.

Example 27

Methyl 5-butyl-1-(1-butyl-1H-indol-2-yl)-5H-pyrido[4,3-b]indole-3-carboxylate (18ea). According to the general procedure mentioned above, 17e (0.100 g, 0.49 mmol), 2a (31 mg, 0.25 mmol) and DIPEA (0.114 mL, 0.88 mmol) were heated in a sealed tube at 120° C. for 3 h. After workup, crude was purified through alumina (neutral, 175 mesh) column chromatography using hexane-EtOAc (85:15) as eluent; Yield 66% (84 mg); Yellow liquid; Rf 0.60 (2:1 hexane-EtOAc); IR (KBr) 3064 (=C—H), 2972-2854 (C—H), 1726 (C=O), 1621-1570 (C=C), 1462-1317 (C—H bend), 796 (=C—H bend) cm-1; $^1$H NMR (400 MHz, CDCl$_3$) δ 8.27 (s, 1H), 8.00 (d, J=8.0 Hz, 1H), 7.72 (d, J=7.5 Hz, 1H), 7.59-7.45 (m, 3H), 7.30 (dd, J=7.6, 7.5 Hz, 1H), 7.18 (dd, J=8.2, 7.2 Hz, 1H), 7.13 (dd, J=8.2, 7.3 Hz, 1H), 6.97 (s, 1H), 4.43 (t, J=6.8 Hz, 2H), 4.34 (t, J=7.0 Hz, 2H), 4.05 (s, 3H), 2.00-1.87 (m, 2H), 1.71-1.60 (m, 2H), 1.52-1.39 (m, 2H), 1.16-1.04 (m, 2H), 0.99 (t, J=7.0 Hz, 3H), 0.62 (t, J=7.3 Hz, 3H); $^{13}$C NMR (100 MHz, CDCl$_3$) δ 167.1, 146.8, 145.4, 142.7, 141.6, 137.7, 136.9, 127.92, 127.87, 123.3, 122.2, 121.3, 120.9, 120.8*, 119.6, 110.2, 109.3, 105.6, 104.7, 52.9, 43.9, 43.4, 32.2, 31.1, 20.6, 20.0, 13.9, 13.5; HRMS (ESI) calcd for [C$_{29}$H$_{31}$N$_3$O$_2$+H$^+$] 454.2489, found 454.2559. *merged carbons.

Example 28

Methyl 5-tosyl-1-(1-tosyl-1H-indol-2-yl)-2,5-dihydro-1H-pyrido[4,3-b]indole-3-carboxylate (18fa). According to the general procedure mentioned above, 17f (0.100 g, 0.33 mmol), 2a (21 mg, 0.17 mmol) and DIPEA (0.101 mL, 0.58 mmol) were heated in a sealed tube at 120° C. for 8 h. After workup, crude was purified through alumina (neutral, 175 mesh) column chromatography using hexane-EtOAc (90: 10) as eluent; Yield 63% (70 mg); Yellow solid; m.p.=205-207° C.; Rf 0.60 (2:1 hexane-EtOAc); IR (ATR) 3413 (N—H), 3062 (=C—H), 2956-2850 (C—H), 1706 (C=O), 1633-1489 (C=C), 1448-1350 (C—H bend), 1307 (N—S=O), 1145 (S=O), 812-687 (=C—H bend) cm-1; $^1$H NMR (400 MHz, CDCl$_3$) δ 8.16 (dd, J=8.0, 8.0 Hz, 2H), 7.73 (d, J=8.5 Hz, 2H), 7.70 (d, J=8.5 Hz, 2H), 7.32-7.26 (m, 3H), 7.24-7.19 (m, 3H), 7.18-7.14 (m, 2H), 7.09 (d, J=2.0 Hz, 1H), 6.98 (dd, J=7.5, 7.3 Hz, 1H), 6.59 (d, J=2.0 Hz, 1H), 6.38 (d, J=7.8 Hz, 1H), 5.90 (s, 1H), 5.64 (s, 1H), 3.83 (s, 3H), 2.41 (s, 3H), 2.37 (s, 3H); $^{13}$C NMR (100 MHz, CDCl3) δ 163.9, 145.4, 145.0, 139.4, 137.7, 137.4, 136.3, 135.2, 135.0, 132.6, 130.1, 129.9, 128.8, 127.7, 126.8, 126.3, 125.2, 124.4, 124.0, 123.8, 121.2, 117.5, 114.9, 114.8, 113.1, 110.6, 94.4, 52.6, 47.9, 21.7, 21.6; HRMS* (ESI) calcd for [C$_{35}$H$_{27}$N$_3$O$_6$S$_2$+H$^+$] 650.1414, found 650.1386. *HRMS peak corresponds to dehydrogenated or aromatized form of compound 18fa.

Example 29

Methyl 4-(furan-2-yl)furo[3,2-c]pyridine-6-carboxylate (20aa). According to the general procedure as mentioned above, 19a (200 mg, 2.08 mmol), 2a (130 mg, 1.04 mmol) and DIPEA (0.670 mL, 3.72 mmol) were heated in a sealed tube at 120° C. for 6 h. After workup, crude was purified through alumina (neutral, 175 mesh) column chromatography using hexane-EtOAc (98:2) as eluent; Yield 50% (126 mg); Off white solid; m.p.=95-97° C.; Rf 0.65 (4:1 hexane-EtOAc); IR (KBr) 3032 (=C—H), 2957-2856 (C—H), 1731 (C=O), 1713-1560 (C=C), 1359 (C—H bend), 1112-993 (C—O), 722 (=C—H bend) cm-1; $^1$H NMR (400 MHz, CDCl$_3$) δ 8.19 (s, 1H), 7.85 (d, J=3.0 Hz, 1H), 7.65 (dd, J=1.9, 0.92 Hz, 1H), 7.45-7.40 (m, 1H), 7.36 (d, J=3.0 Hz, 1H), 6.61 (dd, J=3.5 Hz, 1.9 Hz, 1H), 4.03 (s, 3H); $^{13}$C NMR (100 MHz, CDCl$_3$) δ 166.0, 160.6, 153.2,148.1, 144.2, 143.5, 143.2, 122.7, 112.2, 111.4, 107.9, 106.9, 53.0; HRMS (ESI) calcd for [C$_{13}$H$_9$NO$_4$+Na$^+$] 266.0424, found 266.0417

Example 30

Ethyl 4-(furan-2-yl)furo[3,2-c]pyridine-6-carboxylate (20ab). According to the general procedure as mentioned above, furan-2-carbaldehyde (19a, 200 mg, 2.08 mmol), Glycine ethyl ester hydrochloride (2b, 145 mg, 1.04 mmol) and DIPEA (0.670 mL, 3.72 mmol) were heated in a sealed tube at 120° C. for 6 h. After workup, crude was purified through alumina (neutral, 175 mesh) column chromatography using hexane-EtOAc (99:1) as eluent; Yield 48% (128 mg); Yellow liquid; Rf 0.70 (4:1 hexane-EtOAc); IR (KBr) 3032 (=C—H), 2976-2855 (C—H), 1742 (C=O), 1730-1524 (C=C), 1371 (C—H bend), 1165-1005 (C—O), 741 (=C—H bend) cm-1; $^1$H NMR (400 MHz, CDCl$_3$) δ 8.17 (s, 1H), 7.83 (d, J=2.0 Hz, 1H), 7.64 (m, 1H), 7.42 (dd, J=2.0 Hz, 0.8 Hz, 1H), 7.37 (d, J=3.2 Hz, 1H), 6.60 (dd, J=3.3 Hz, 1.8 Hz, 1H), 4.49 (q, J=7.3 Hz, 2H), 1.47 (t, J=7.3 Hz, 3H); $^{13}$C NMR (400 MHz, CDCl3) δ 165.4, 160.7, 153.4, 148.1, 144.1, 143.6, 143.5, 122.5, 112.3, 111.4, 107.8, 106.9, 62.0, 14.4; HRMS (ESI) calcd for [C$_{14}$H$_{11}$NO$_4$+Na$^+$] 280.0580, found 280.0571.

Example 31

Tert-butyl-4-(furan-2-yl)furo[3,2-c]pyridine-6-carboxylate (20ac). According to the general procedure mentioned above, 19a (200 mg, 2.08 mmol), 2c (175 mg, 1.04 mmol) and DIPEA (0.670 mL, 3.72 mmol) were heated in a sealed tube at 120° C. for 7 h. After workup, crude was purified through alumina (neutral, 175 mesh) column chromatography using hexane-EtOAc (99:1) as eluent; Yield 46% (136 mg); Off white solid; m.p.=78-80° C.; Rf 0.70 (4:1 hexane-EtOAc); IR (KBr) 3032 (=C—H), 2976-2855 (C—H), 1742 (C=O), 1730-1524 (C=C), 1371 (C—H bend), 1165-1005 (C—O), 741 (=C—H bend) cm-1; $^1$H NMR (400 MHz, CDCl$_3$) δ 8.08 (s, 1H), 7.82 (d, J=3.0 Hz, 1H), 7.63 (dd, J=1.5, 0.5 Hz, 1H), 7.43 (dd, J=2.0 Hz, 0.8 Hz, 1H), 7.39 (d, J=3.0 Hz, 1H), 6.60 (dd, J=3.5 Hz, 1.8 Hz, 1H), 1.66 (s, 9H); $^{13}$C NMR (400 MHz, CDCl3) δ 164.0, 160.7, 153.7, 147.9, 144.6, 143.9, 143.4, 122.2, 112.2, 111.2, 107.4, 106.9, 82.0, 28.2; HRMS (ESI) calcd for [C$_{16}$H$_{15}$NO$_4$+Na$^+$] 308.0893, found 308.0890.

Example 32

Methyl 2-methyl-4-(5-methylfuran-2-yl)furo[3,2-c]pyridine-6-carboxylate (20ba). According to the general procedure mentioned above, 5-Methylfuran-2-carbaldehyde (19b, 200 mg, 1.82 mmol), Glycine methyl ester hydrochloride (2a, 114 mg, 0.91 mmol) and DIPEA (0.555 mL, 3.18 mmol) were heated in a sealed tube at 120° C. for 6 h. After workup, crude was purified through alumina (neutral, 175 mesh) column chromatography using hexane-EtOAc (99:1) as eluent; Yield 54% (133 mg); Off white solid; m.p.=78-80° C.; Rf 0.70 (4:1 hexane-EtOAc); IR (KBr) 3032 (=C—H), 2976-2855 (C—H), 1742 (C=O), 1730-1524 (C=C), 1371 (C—H bend), 1165-1005 (C—O), 741 (=C—H bend) cm-1; $^1$H NMR (400 MHz, CDCl$_3$) δ 8.04 (s, 1H), 7.17 (d, J=3.0 Hz, 1H), 6.96 (s, 1H), 6.18 (d, J=3.0 Hz, 1H), 4.00 (s, 3H), 2.55 (s, 3H), 2.45 (s, 3H); 13C NMR (400 MHz, CDCl$_3$) δ 166.2, 160.3, 159.4, 154.2, 151.5, 142.3, 142.2, 124.0, 112.3, 108.5, 106.8, 102.9, 52.8, 14.2, 14.0.

Example 33

(2-Methyl-4-(5-methylfuran-2-yl)furo[3,2-c]pyridin-6-yl)methanol (21). In a two-neck round-bottom flask (50 mL), Methyl 2-methyl-4-(5-methylfuran-2-yl)furo[3,2-c] pyridine-6-carboxylate (20ba, 0.250 gms, 0.92 mmol) was dissolved in dry THF (5 mL) under an inert atmosphere. The reaction mixture was cooled to 0° C. and solid LiAlH4 (0.104 gms, 2.76 mmol) was cautiously added to it, in a single portion. The reaction mixture was allowed to warm to room temperature and stirred for 20 min The reaction progress was monitored through TLC. The reaction mixture was again cooled to 0° C. to quench excess LiAlH$_4$ by adding saturated NH$_4$Cl (10 mL) solution. The aqueous layer was extracted using EtOAc (10×3 mL) and combined organic extracts were dried over anhydrous Na$_2$SO$_4$. Crude was filtered and solvent was evaporated under reduced pressure. Residue was purified over neutral alumina (175 mesh) column chromatography using hexane-EtOAc (80:20) as eluent; Yield 66% (148 mg); Yellow liquid; Rf 0.45 (1:1 hexane-EtOAc); $^1$H NMR (400 MHz, CDCl3) δ 7.15-7.05 (m, 2H), 6.90 (s, 1H), 6.17 (d, J=1.7 Hz, 1H), 4.80 (s, 2H), 2.50 (s, 3H), 2.45 (s, 3H); $^{13}$C NMR (400 MHz, CDCl$_3$) δ 161.2, 156.7, 153.8, 153.2, 152.3, 140.9, 120.4, 111.1, 108.3, 102.3, 100.9, 64.3, 14.04, 14.01.

Example 34

2-Methyl-4-(5-methylfuran-2-yl)-6-((prop-2-yn-1-yloxy) methyl)furo[3,2-c]pyridine (22). In a two-neck round-bottom flask (50 mL), (2-Methyl-4-(5-methylfuran-2-yl)furo[3,2-c]pyridin-6-yl)methanol (21, 70 mg, 0.29 mmol) was dissolved in dry DMF (2 mL) under an inert atmosphere. The reaction mixture was cooled to 0° C. and sodium hydride (55-60% suspension in mineral oil, 14 mg, 0.35 mmol) was added to it, in a single portion. The reaction mixture was stirred for 20 min at the same temperature. Propargyl bromide (80% in toluene, 33 μL, 0.35 mmol) was added drop-wise through a micro-pipette. The reaction mixture was allowed to warm to room temperature and further stirred for 3 h. The reaction progress was monitored through TLC. The reaction mixture was briefly cooled before quenching the reaction by adding brine water (5 mL). The aqueous layer was extracted with EtOAc (10×3 mL) and the combined organic extracts were dried over anhydrous Na$_2$SO$_4$. Crude was filtered and solvent was evaporated under reduced pressure. The residue was purified over neutral alumina (175 mesh) column chromatography using hexane-EtOAc (97:3) as eluent; Yield 70% (57 mg); Yellow oily liquid; Rf 0.70 (7:3 hexane-EtOAc).

Example 35

1-(2-(4-(((2-Methyl-4-(5-methylfuran-2-yl)furo[3,2-c] pyridin-6-yl)methoxy)methyl)-1H-1,2,3-triazol-1-yl)ethyl)

indoline-2,3-dione (26). In a round bottom flask (25 mL), 2-Methyl-4-(5-methylfuran-2-yl)-6-((prop-2-yn-1-yloxy)methyl)furo[3,2-c]pyridine (22, 30 mg, 0.11 mmol) and 1-(2-Azidoethyl)indoline-2,3-dione (25, 24 mg, 0.11 mmol) were dissolved in DMF (2 mL). Under an inert atmosphere, Copper (II) acetate (monohydrated, 12 mg, 0.06 mmol) was added in one portion to the above solution at room temperature. The reaction mixture was stirred at ambient temperature for another 24 h. Reaction progress was monitored through TLC. Brine water (5 mL) was added to quench the reaction and the aqueous layer was extracted by EtOAc (5×3 mL). The combined organic extracts were dried over anhydrous Na2SO4. Crude was filtered and excess solvent was evaporated under reduced pressure. The residue was purified over neutral alumina (175 mesh) column chromatography using $CH_2Cl_2$-MeOH (95:5) solvent mixture as eluent; Yield 82% (45 mg); Yellow-orange liquid; Rf 0.25 (1:3 hexane-EtOAc); $^1$H NMR (400 MHz, CDCl$_3$) δ 7.62 (s, 1H), 7.51 (d, J=7.5 Hz, 1H), 7.45 (dd, J=7.8, 7.5 Hz, 1H), 7.25 (s, 1H), 7.05-6.95 (m, 2H), 6.87 (s, 1H), 6.52 (d, J=8.0 Hz, 1H), 6.17 (d, J=2.8 Hz, 1H), 4.75-4.68 (m, 4H), 4.67 (s, 2H), 4.25 (t, J=5.8 Hz, 2H), 2.52 (s, 3H), 2.45 (s, 3H); HRMS (ESI) calcd for [$C_{27}H_{23}N_5O_5$+Na+] 520.1591, found 520.1595.

Example 36

Methyl 1-(benzofuran-2-yl)benzofuro[3,2-c]pyridine-3-carboxylate (28aa). According to the general procedure mentioned above, 27 (100 mg, 0.68 mmol), 2a (43 mg, 0.34 mmol) and DIPEA (0.240 mL, 1.36 mmol) were heated in a sealed tube at 120° C. for 6 h. After workup, crude was purified through alumina (neutral, 175 mesh) column chromatography using hexane-EtOAc (98:2) as eluent; Yield 60% (70 mg); Yellow-orange solid; m.p. =163-165° C.; Rf 0.40 (8:2 hexane-EtOAc); IR (KBr) 3065 (=C—H), 2948-2850 (C—H), 1720 (C=O), 1612-1539 (C=C), 1350-1338 (C—H bend), 1256-1094 (C—O), 735 (=C—H bend) cm-1; $^1$H NMR (400 MHz, CDCl$_3$) δ 8.85 (d, J=7.8 Hz, 1H), 8.30 (s, 1H), 7.81 (s, 1H), 7.78-7.71 (m, 2H), 7.69 (d, J=8.0 Hz, 1H), 7.63 (dd, J=8.0, 7.3 Hz, 1H), 7.51 (dd, J=7.6, 7.5 Hz, 1H), 7.44 (dd, J=7.8, 7.5 Hz, 1H), 7.34 (dd, J=7.6, 7.5 Hz, 1H), 4.08 (s, 3H); $^{13}$C NMR (400 MHz, CDCl$_3$) δ 165.5, 162.7, 157.4, 155.4, 154.5, 145.4, 144.3, 129.6, 128.4, 125.7, 125.6, 124.3, 123.7, 122.1, 120.9, 120.8, 111.9, 111.5, 108.7, 108.4, 53.1; HRMS (ESI) calcd for [$C_{21}H_{13}NO_4$+Na$^+$] 366.0737, found 366.0693.

Example 37

Ethyl 1-(benzofuran-2-yl)benzofuro[3,2-c]pyridine-3-carboxylate (28ab). According to the general procedure mentioned above, 27 (100 mg, 0.68 mmol), 2b (48 mg, 0.34 mmol) and DIPEA (0.240 mL, 1.36 mmol) were heated in a sealed tube at 120° C. for 6 h. After workup, crude was purified through alumina (neutral, 175 mesh) column chromatography using hexane-EtOAc (98:2) as eluent; Yield 55% (67 mg); Yellow solid; m.p.=141-143° C.; Rf 0.40 (8:2 hexane-EtOAc); IR (KBr) 3065 (=C—H), 2987-2850 (C—H), 1714 (C=O), 1625-1540 (C=C), 1367-1340 (C—H bend), 1266-1097 (C—O), 750 (=C—H bend) cm-1; $^1$H NMR (400 MHz, CDCl3) δ 8.85 (d, J=8.0 Hz, 1H), 8.26 (s, 1H), 7.81 (s, 1H), 7.75 (d, J=8.0 Hz, 1H), 7.72 (d, J=7.8 Hz, 1H), 7.67 (d, J=8.3 Hz, 1H), 7.61 (dd, J=8.0, 7.5 Hz, 1H), 7.49 (dd, J=8.0, 8.3 Hz, 1H), 7.43 (dd, J=7.8, 7.5 Hz, 1H), 7.34 (dd, J=8.0, 8.3 Hz, 1H), 4.54 (q, J=7.1 Hz, 2H), 1.51 (t, J=7.1 Hz, 3H); $^{13}$C NMR (100 MHz, CDCl3) δ 164.9, 162.8, 157.4, 155.5, 154.7, 145.8, 144.3, 129.6, 128.5, 125.74, 125.73, 124.3, 123.7, 122.2, 121.0, 120.7, 111.9, 111.6, 108.7, 108.3, 62.2, 14.4; HRMS (ESI) calcd for [$C_{22}H_{15}NO_4$+Na+] 380.0893, found 380.0844.

Example 38

Tert-butyl 1-(benzofuran-2-yl)benzofuro[3,2-c]pyridine-3-carboxylate (28ac). According to the general procedure mentioned above, 27 (100 mg, 0.68 mmol), 2c (57 mg, 0.34 mmol) and DIPEA (0.240 mL, 1.36 mmol) were heated in a sealed tube at 120° C. for 7 h. After workup, crude was purified through alumina (neutral, 175 mesh) column chromatography using hexane-EtOAc (98:2) as eluent; Yield 45% (64 mg); Yellow solid; m.p.=100-102° C.; Rf 0.40 (8:2 hexane-EtOAc); IR (KBr) 3060 (=C—H), 2977-2851 (C—H), 1715 (C=O), 1626-1540 (C=C), 1365-1340 (C—H bend), 1273-1074 (C—O), 738 (=C—H bend) cm-1; $^1$H NMR (400 MHz, CDCl$_3$) δ 8.88 (d, J=8.0 Hz, 1H), 8.18 (s, 1H), 7.83 (s, 1H), 7.74 (d, J=7.8 Hz, 1H), 7.71 (d, J=8.3 Hz, 1H), 7.65 (d, J=8.0 Hz, 1H), 7.59 (dd, J=8.0, 7.3 Hz, 1H), 7.48 (dd, J=7.6, 7.5 Hz, 1H), 7.42 (dd, J=8.3, 7.3 Hz, 1H), 7.33 (dd, J=7.5, 7.3 Hz, 1H), 1.71 (s, 9H); $^{13}$C NMR (100 MHz, CDCl$_3$) δ 163.6, 162.8, 157.4, 155.4, 154.9, 146.8, 144.1, 129.3, 128.5, 125.7, 125.6, 124.2, 123.6, 122.1, 121.0, 120.2, 111.8, 111.5, 108.6, 107.9, 82.4, 28.2; HRMS (ESI) calcd for [$C_{24}H_{19}NO_4$+Na$^+$] 408.1206, found 408.1153.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

We claim:
1. A compound of Formula I

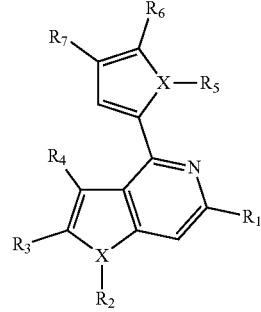

Formula I and its prodrug, stereoisomer, racemate, salt, hydrate, salt hydrate, acid salt hydrate, solvate, an isomorphic crystalline form, and compositions thereof;
wherein, 'X' is one of nitrogen or oxygen;
$R_1$ is one of morpholino methanone, —CONH$_2$, —CN, —CHO, —COOH, —ROH, —COOR wherein R is an alkyl group R2 and R5 is at least one independently selected from a group consisting of —H, -Boc, alkyl, tosyl, phenyl sulfonyl, aryloxy, benzyloxy, optionally substituted benzyl, and optionally substituted aryl; and R3, R4, R6 and R7 is at least one independently selected from —H, alkyl group, or R3 and R4, and R6 and R7, may be fused to form an optionally substituted benzene ring.

2. The compound of Formula I as claimed in claim 1, wherein X is nitrogen; R1 is one of morpholino methanone, —CONH2, —CN, —CHO, —COOH, —ROH, and —COOR wherein R is an alkyl group selected from a group consisting of -Me, Et, or ᵗBu; R2 and R5 are identical and are selected from a group consisting of hydrogen, methyl, benzyl, methoxy benzyl, tosyl, and phenyl sulfonyl; and R3, R4, R6 and R7 is one independently selected from —H, or —CH3.

3. The compound of Formula I as claimed in claim 1, wherein X is nitrogen; R1 is one of morpholino methanone, —CONH2, —CN, —CHO, —COOH, —ROH, and —COOR wherein R is an alkyl group selected from a group consisting of -Me, Et, or ᵗBu; R2 and R5 are identical and are selected from a group consisting of hydrogen, methyl, benzyl, methoxy benzyl, tosyl, and phenyl sulfonyl, R3 and R4, and R6 and R7, may be fused to form an optionally substituted benzene ring.

4. The compound of Formula I as claimed in claim 1, is

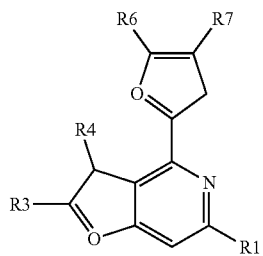

wherein R1 is —COOR wherein R is an alkyl group selected from a group consisting of -Me, Et, or ᵗBu; R3, R4, R6 and R7 is at least one independently selected from —H, alkyl group, or R3 and R4, and R6 and R7, may be fused to form an optionally substituted benzene ring.

5. A compound of Formula II

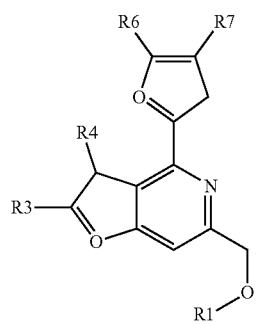

and its prodrug, stereoisomer, racemate, salt, hydrate, salt hydrate, acid salt hydrate, solvate, an isomorphic crystalline form, and compositions thereof; wherein, R1 is an optionally substituted isatin, R3, R4, R6 and R7 is at least one independently selected from —H, alkyl group, or R3 and R4, and R6 and R7, may be fused to form an optionally substituted benzene ring.

6. The compound of Formula II as claimed in claim 5 is

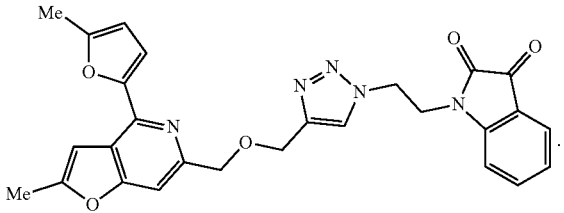 [SMILES: Cc1ccc(-c2nc(COCc3cn(CCN4C(=O)C(=O)c5ccccc54)nn3)cc3oc(C)cc23)o1]

7. The compound of Formula I as claimed in claim 1, is selected from the group consisting of:
a) methyl 1-benzyl-4-(1-benzyl-1H-pyrrol-2-yl)-1H-pyrrolo[3,2-c]pyridine-6-carboxylate;
b) methyl 1-(4-methoxybenzyl)-4-(1-(4-methoxybenzyl)-1H-pyrrol-2-yl)-1H-pyrrolo[3,2-c]pyridine-6-carboxylate;
c) methyl 1-methyl-4-(1-methyl-1H-pyrrol-2-yl)-1H-pyrrolo[3,2-c]pyridine-6-carboxylate;
d) tert-butyl 1-benzyl-4-(1-benzyl-1H-pyrrol-2-yl)-1H-pyrrolo[3,2-c]pyridine-6-carboxylate;
e) ethyl 1-methyl-4-(1-methyl-1H-pyrrol-2-yl)-1H-pyrrolo[3,2-c]pyridine-6-carboxylate;
f) ethyl 1-benzyl-4-(1-benzyl-1H-pyrrol-2-yl)-1H-pyrrolo[3,2-c]pyridine-6-carboxylate;
g) ethyl 1-(4-methoxybenzyl)-4-(1-(4-methoxybenzyl)-1H-pyrrol-2-yl)-1H-pyrrolo[3,2-c]pyridine-6-carboxylate;
h) tert-butyl 1-(4-methoxybenzyl)-4-(1-(4-methoxybenzyl)-1H-pyrrol-2-yl)-1H-pyrrolo[3,2-c]pyridine-6-carboxylate;
i) methyl 1-tosyl-4-(1-tosyl-1H-pyrrol-2-yl)-1H-pyrrolo[3,2-c]pyridine-6-carboxylate;
j) methyl 1-(phenylsulfonyl)-4-(1-(phenylsulfonyl)-1H-pyrrol-2-yl)-1H-pyrrolo[3,2-c]pyridine-6-carboxylate;
k) methyl 1-benzyl-4-(1-benzyl-5-methyl-1H-pyrrol-2-yl)-2-methyl-1H-pyrrolo[3,2-c]pyridine-6-carboxylate;
l) 1-benzyl-4-(1-benzyl-1H-pyrrol-2-yl)-1H-pyrrolo[3,2-c]pyridine-6-carboxamide;
m) 1-benzyl-4-(1-benzyl-1H-pyrrol-2-yl)-1H-pyrrolo[3,2-c]pyridine-6-carbonitrile;
n) (1-benzyl-4-(1-benzyl-1H-pyrrol-2-yl)-1H-pyrrolo[3,2-c]pyridin-6-yl)methanol;
o) 1-benzyl-4-(1-benzyl-1H-pyrrol-2-yl)-1H-pyrrolo[3,2-c]pyridine-6-carbaldehyde;
p) 1-methyl-4-(1-methyl-1H-pyrrol-2-yl)-1H-pyrrolo[3,2-c]pyridine-6-carboxylic acid
q) (1-methyl-4-(1-methyl-1H-pyrrol-2-yl)-1H-pyrrolo[3,2-c]pyridin-6-yl)(morpholino) methanone;
r) methyl 5-methyl-1-(1-methyl-1H-indol-2-yl)-5H-pyrido[4,3-b]indole-3-carboxylate;
s) ethyl 5-methyl-1-(1-methyl-1H-indol-2-yl)-5H-pyrido[4,3-b]indole-3-carboxylate;
t) tert-butyl 5-methyl-1-(1-methyl-1H-indol-2-yl)-5H-pyrido[4,3-b]indole-3-carboxylate;
u) methyl 4-(furan-2-yl)furo[3,2-c]pyridine-6-carboxylate;
v) tert-butyl-4-(furan-2-yl)furo[3,2-c]pyridine-6-carboxylate;

w) methyl 1-(benzofuran-2-yl)benzofuro[3,2-c]pyridine-3-carboxylate;

x) ethyl 1-(benzofuran-2-yl)benzofuro[3,2-c]pyridine-3-carboxylate; and y) tert-butyl 1-(benzofuran-2-yl)benzofuro[3,2-c]pyridine-3-carboxylate.

8. The compound of Formula I as claimed in claim 1 has anti-bacterial and anti-cancer activity.

9. A pharmaceutical composition comprising a therapeutically effective amount of the compound of Formula I as claimed in claim 1, and at least one component selected from a group consisting of carriers, diluents, excipients and combinations thereof.

10. A process for preparation of compound of Formula I as claimed in claim 1, the process comprising: contacting a reactant selected from a group consisting of N-substituted pyrrole-2-carboxaldehyde, N-substituted indole-carboxaldehyde, optionally substituted furfural, and benzofuran-2-carboxaldehyde with an acid salt of glycine alkyl ester in the presence of a base at a temperature range of 100-160° C. for a period of 3-15 hours to obtain the compound of Formula I.

11. A process for preparation of compound of Formula II as claimed in claim 5 comprises the steps of:

a) contacting an optionally substituted furfural with an acid salt of glycine alkyl ester in the presence of a base at a temperature range of 100-160° C. for a period of 3-15 hours to obtain the compound of Formula I;

b) reacting the compound of Formula I in the presence of a reducing agent under first reaction conditions to yield a corresponding alcohol;

c) propargylation of the corresponding alcohol obtain in step a) under second reaction conditions to obtain a corresponding alkyne derivative; and d) allowing a copper catalyzed click reaction between the corresponding alkyne derivative as obtained in step b) with an isatin azide under third reaction conditions to obtain the compound of Formula II.

12. The process as claimed in claim 10 or 11, wherein the base is at least one selected from a group consisting of N,N-Diisopropylethylamine (DIPEA), triethylamine (Et$_3$N), K$_2$CO$_3$, NAH, Cs$_2$CO$_3$, and 1,8-Diazabicyclo[5.4.0]undec-7-ene (DBU).

13. The process as claimed in claim 10 or 11, wherein the molar ratio of the reactant to the acid salt of glycine alkyl ester is in the range of 1:2 to 2:1, and wherein the molar ratio of the reactant to the base is in the range of 1:1 to 1:15.

14. The process as claimed in claim 11, wherein the first reaction conditions include LiAlH$_4$ as the reducing agent in THF at a temperature range of 0° C.-30° C. for a period of 10-30 minutes; the second reaction conditions include propargylation with propargyl bromide and sodium hydride in refluxing anhydrous THF in the presence of a catalyst for a period of 2-4 hours, wherein the catalyst is tetrabutylammonium iodide (TBAI); and the third reaction conditions include a temperature range of 20° C.-35° C for a period of 25-35 hours.

* * * * *